(12) United States Patent
Zhang et al.

(10) Patent No.: US 8,129,477 B1
(45) Date of Patent: Mar. 6, 2012

(54) MEDICAL DEVICES AND METHODS INCLUDING BLENDS OF BIODEGRADABLE POLYMERS

(75) Inventors: Jianbin Zhang, Minneapolis, MN (US); SuPing Lyu, Maple Grove, MN (US); James Louis Schley, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 460 days.

(21) Appl. No.: 12/534,264

(22) Filed: Aug. 3, 2009

Related U.S. Application Data

(60) Provisional application No. 61/086,707, filed on Aug. 6, 2008.

(51) Int. Cl.
*C08L 67/04* (2006.01)

(52) U.S. Cl. ......... 525/418; 528/354; 528/361; 523/124

(58) Field of Classification Search .................. 525/418; 528/354, 361; 523/124
See application file for complete search history.

(56) References Cited

U.S. PATENT DOCUMENTS

| | | | |
|---|---|---|---|
| 4,844,854 A | 7/1989 | Kaplan et al. | |
| 5,252,642 A | 10/1993 | Sinclair et al. | |
| 5,641,501 A | 6/1997 | Cooper et al. | |
| 5,756,651 A * | 5/1998 | Chen et al. | 528/354 |
| 5,871,468 A | 2/1999 | Kramer et al. | |
| 6,150,493 A | 11/2000 | Hait et al. | |
| 6,221,316 B1 * | 4/2001 | Hanggi et al. | 422/549 |
| 6,400,992 B1 | 6/2002 | Borgersen et al. | |
| 6,434,430 B2 | 8/2002 | Borgersen et al. | |
| 6,607,548 B2 | 8/2003 | Pohjonen et al. | |
| 6,926,903 B2 | 8/2005 | Pirhonen et al. | |
| 2003/0104029 A1 | 6/2003 | Pirhonen et al. | |
| 2003/0105530 A1 | 6/2003 | Pirhonen et al. | |
| 2006/0041102 A1 | 2/2006 | Hossainy et al. | |
| 2006/0247389 A1 | 11/2006 | Shaikh et al. | |
| 2007/0117950 A1 | 5/2007 | Jayakannan et al. | |
| 2007/0182041 A1 * | 8/2007 | Rizk et al. | 264/6 |
| 2007/0231365 A1 | 10/2007 | Wang et al. | |
| 2007/0253996 A1 | 11/2007 | Bin et al. | |
| 2008/0033540 A1 | 2/2008 | Wang et al. | |
| 2008/0063685 A1 | 3/2008 | Wang et al. | |

FOREIGN PATENT DOCUMENTS

| | | |
|---|---|---|
| EP | 1 837 042 | 9/2007 |
| WO | WO 00/01426 | 1/2000 |
| WO | WO 03/064531 A1 | 8/2003 |
| WO | WO 2005/014718 A1 | 2/2005 |
| WO | WO 2007/020430 A2 | 2/2007 |
| WO | WO 2007/020432 | 2/2007 |
| WO | WO 2007/092417 | 8/2007 |
| WO | WO 2007/110611 A1 | 10/2007 |
| WO | WO 2007/134222 | 11/2007 |

OTHER PUBLICATIONS

Ignatov et al., "PET/PC Blends and Copolymers by One-step Extrusion: Chemical Structure and Physical Properties of 50/50 Blends", Polymer, 38 (t): 195-200, 1997.

(Continued)

*Primary Examiner* — Alicia Toscano

(57) ABSTRACT

Implantable medical devices and methods including blends of biodegradable polymers are disclosed herein. The polymer blends include a continuous phase in which the polymer chains are oriented along an axis. Such polymer blends can exhibit properties such as improved toughness that can be desirable for use in medical devices.

20 Claims, 43 Drawing Sheets

OTHER PUBLICATIONS

Ignatov et al, "PET/PC Blends and Copolymers by One-step Extrusion: Influence of the Initial Polymer Composition and Type of Catalyst", Polymer, 38 (1): 201-205, 1997.

Jayakannan et al., "Mechanistic Aspects of Ester-Carbonate Exchange in Polycarbonate/Cycloaliphatic Polyester with Model Reactions", Journal of Polymer Science: Part A: Polymer Chemistry, 42: 3996-4008, 2004.

Qin et al., "Use of Polylactic Acid Polytrimethylene Carbonate Blends Membrane to Prevent Postoperative Adhesions", Journal of Biomedical Materials Research Part B: Applied Biomaterials DOI 10.1002/jbmb.

Sodergard et al., "Properties of Lactic Acid Based Polymers and Their Correlation with Composition", Prog. Polym Sci, 27: 1123-1163, 2002.

Zhang et al., Synthesis and drug release behavior of poly (trimethylene carbonate)-poly(ethylene, glycol)-poly(trimethylene carbonate) nanoparticles, Biomaterials, 26:2089-2094, 2005.

* cited by examiner

C

D

MEDICAL DEVICES AND METHODS INCLUDING BLENDS OF BIODEGRADABLE POLYMERS

This application claims priority to U.S. provisional patent application Ser. No. 61/066,707, filed on Aug. 6, 2008, the contents of which are hereby incorporated by reference in their entirety.

BACKGROUND

Biodegradable polymers have found use in a wide variety of applications ranging from trash bags that decompose in landfills to implantable medical devices that biodegrade in the body. Most of these applications require that such polymers have adequate physical properties and stability to provide for suitable handling and utility prior to being subjected to end use conditions that promote biodegradation. Further, it is often preferable that these same polymers rapidly or controllably biodegrade once subjected to such end use conditions. In addition, it is often desired that biodegradable polymers used for implantable medical devices be converted under physiological conditions to materials that do not irritate or harm the surrounding tissue. Many biodegradable polymers known in the art lack the combination of physical and/or chemical properties desired to meet the needs for specific applications.

For example, polylactide homopolymers (e.g., poly-L-lactide; PLA) and copolymers (e.g., poly(L-lactide-co-glycolide; PLGA) have been evaluated for use in making resorbable medical devices (e.g., vascular stents) because such polymers can offer sufficiently high tensile properties (e.g., modulus) at body temperature to allow for implantation of the medical device, and can biodegrade after implantation in the body. However, the use of such polylactides in implantable medical devices is practically limited by their brittleness.

There is a continuing need for new materials and methods having useful properties for making medical devices.

SUMMARY

Brittle polymers can sometimes be blended with polymers that are softer at the temperature of use to reduce the brittleness. For example, polylactide homopolymers (e.g., poly-L-lactide; PLA) and copolymers (e.g., poly(L-lactide-co-glycolide; PLGA) can be blended with materials that are softer at body temperature (e.g., poly(trimethylene carbonate) (PTMC) polycaprolactone (PCL), and/or polyhydroxybutyrate) to reduce the brittleness associated with the polylactides. However, the reduction in brittleness often comes at the expense of reduced tensile properties (e.g., modulus).

The present disclosure provides polymer blends and methods of making and using polymer blends that can have properties suitable for use in medical devices.

In one aspect, the present disclosure provides an implantable medical device that includes a polymer blend. The polymer blend includes: a first phase that is continuous and a second phase that is phase-separated from the first continuous phase. The first continuous phase has a glass transition temperature of at least 40° C. and includes a first biodegradable polymer having chains (e.g., a polylactide homopolymer or copolymer). The chains of the first biodegradable polymer are oriented along an axis. The second phase has a glass transition temperature of 15° C. or less and includes a second biodegradable polymer (e.g., a polymer selected from the group consisting of poly(trimethylene carbonate) (PTMC), polycaprolactone (PCL), polyhydroxybutyrate, and combinations thereof).

In some embodiments, the modulus of the polymer blend parallel to the axis of orientation is at least 100% of the modulus of the first biodegradable polymer; and the strain at break of the polymer blend parallel to the axis of orientation is at least 120% of the strain at break of the first biodegradable polymer.

In other embodiments, the modulus of the polymer blend parallel to the axis of orientation is at least 90% of the modulus of the first biodegradable polymer; the strain at break of the polymer blend parallel to the axis of orientation is at least 120% of the strain at break of the first biodegradable polymer; and the polymer blend includes at least 5% by weight of the second phase, based on the total weight of the polymer blend.

In other certain embodiments, the modulus of the polymer blend parallel to the axis of orientation is at least 80% of the modulus of the first biodegradable polymer; the strain at break of the polymer blend parallel to the axis of orientation is at least 120% of the strain at break of the first biodegradable polymer; and the polymer blend includes at least 20% by weight of the second phase, based on the total weight of the polymer blend.

In another aspect, the present disclosure provides a method of preparing an implantable medical device. The method includes: blending (e.g., melt blending) components including a first biodegradable polymer having chains and a second biodegradable polymer under conditions effective to form a polymer blend. The polymer blend includes: a first phase that is continuous and a second phase that is phase-separated from the first continuous phase. The first continuous phase has a glass transition temperature of at least 40° C. and includes the first biodegradable polymer. The second phase has a glass transition temperature of 15° C. or less and includes the second biodegradable polymer. The method further includes stretching (e.g., melt stretching) the polymer blend under conditions effective to orient the chains of the first biodegradable polymer along the axis of stretching; optionally quenching the stretched polymer blend; and forming a medical device from the stretched and optionally quenched polymer blend.

In some embodiments, the modulus of the stretched and optionally quenched polymer blend parallel to the axis of stretching is at least 100% of the modulus of the first biodegradable polymer; and the strain at break of the stretched and optionally quenched polymer blend parallel to the axis of stretching is at least 120% of the strain at break of the first biodegradable polymer.

In other embodiments, the modulus of the stretched and optionally quenched polymer blend parallel to the axis of stretching is at least 90% of the modulus of the first biodegradable polymer; the strain at break of the stretched and optionally quenched polymer blend parallel to the axis of stretching is at least 120% of the strain at break of the first biodegradable polymer; and the polymer blend includes at least 5% by weight of the second phase, based on the total weight of the polymer blend.

In other certain embodiments, the modulus of the stretched and optionally quenched polymer blend parallel to the axis of stretching is at least 80% of the modulus of the first biodegradable polymer; the strain at break of the stretched and optionally quenched polymer blend parallel to the axis of stretching is at least 120% of the strain at break of the first biodegradable polymer; and the polymer blend includes at least 20% by weight of the second phase, based on the total weight of the polymer blend.

The medical devices and methods of making the disclosed devices can be advantageous in that for at least some embodiments, desirable combinations of properties can be obtained using readily available polymers that are commonly accepted as being suitable for use in medical devices. Desirable combinations of properties can include biodegradability, rigidity (e.g., modulus), strength (e.g., ultimate tensile strength), toughness (e.g., strain at break), and combinations thereof.

The terms "comprises" and variations thereof do not have a limiting meaning where these terms appear in the description and claims.

As used herein, "a," "an," "the," "at least one," and "one or more" are used interchangeably.

As used herein, the term "or" is generally employed in the sense as including "and/or" unless the context of the usage clearly indicates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

FIG. 2 includes graphical representations of Young's modulus (GPa; left y-axis, solid squares) and strain at break (%; right y-axis, open squares) for PLGA and PLGA:PTMC blends at various stretching (%) values parallel to stretching direction.

FIG. 4 includes graphical representations of Young's modulus (solid squares, left y-axis) and strain at break (open squares, right y-axis) for PLGA and PLGA:PTMC blends at various stretching (%) values perpendicular to stretching direction.

FIG. 6A shows various PTMC molecular weights (kg/mole; x-axis), and FIG. 6B shows various mixing times (minutes; x-axis). FIG. 6C shows various stretching temperatures (° C.; x-axis), and FIG. 6D shows various stretching rates (inches/minute; x-axis).

FIG. 7 represents transmission electron micrographs showing microstructures of unstretched PLGA:PTMC blends for various PTMC contents. Samples were stained with $RuO_4$ to show PTMC domains as dark areas.

As shown in FIG. 9, the PTMC domains in a PLGA:PTMC (80:20) blend were stretched to shapes elongated in the stretching direction.

DETAILED DESCRIPTION OF ILLUSTRATIVE EMBODIMENTS

Figure 1:
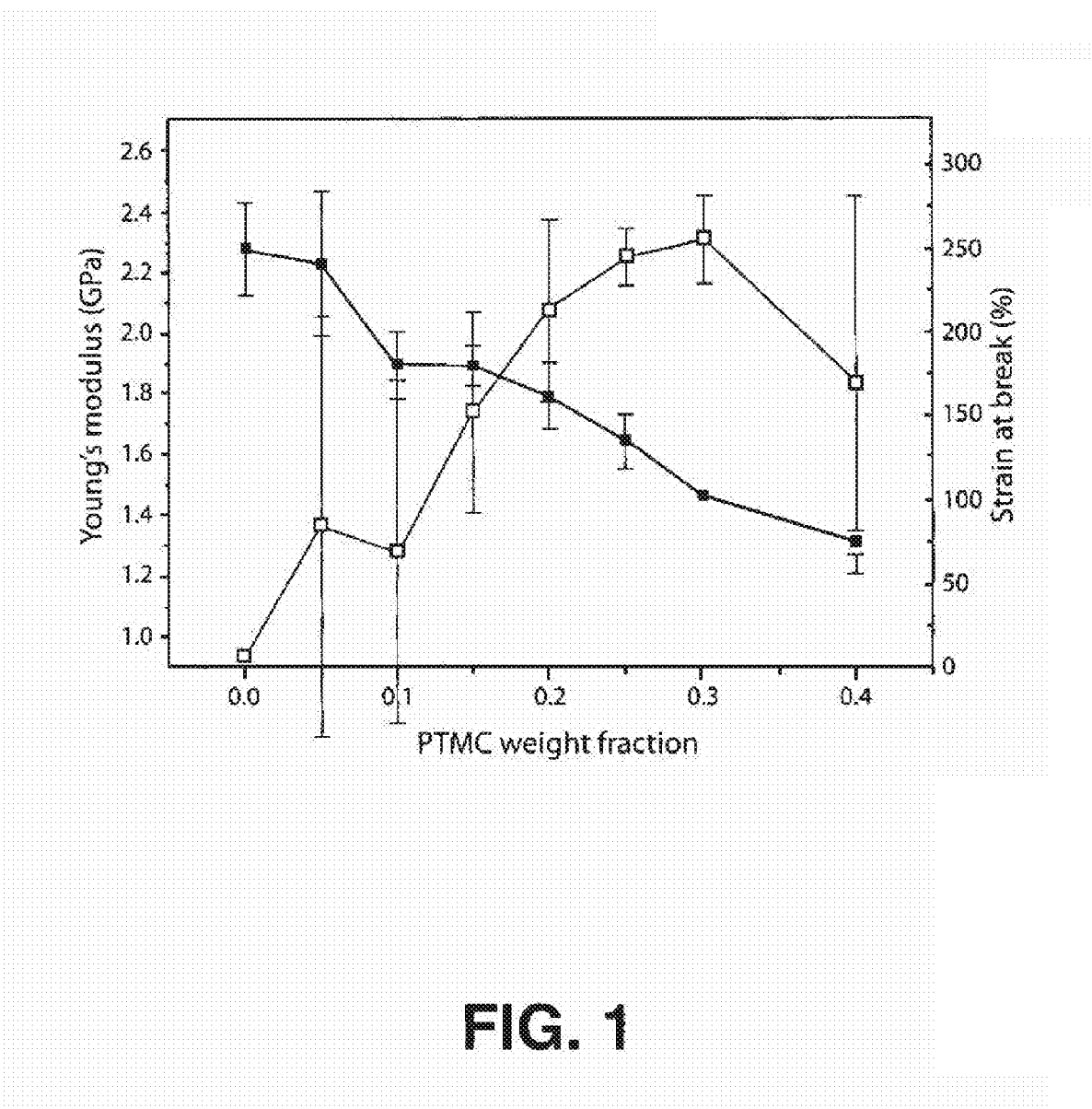
FIG. 1 is a graphical representation showing Young's modulus (GPa; left y-axis, solid squares) and strain at break (%; right y-axis, open squares) for unstretched PLGA and each unstretched PLGA:PTMC blend as a function of the weight fraction PTMC (x-axis).

The present disclosure provides polymer blends and methods of making and using polymer blends that can have properties suitable for use in medical devices. Such properties can include, for example, one or more of biodegradability, rigidity (e.g., modulus), strength (e.g., ultimate tensile strength), toughness (e.g., strain at break), and combinations thereof.

In one aspect, the present disclosure provides an implantable medical device that includes a polymer blend. As used herein, the term "polymer blend" is intended to refer to at least two intimately mixed polymers that are typically homogeneous on the macroscopic level.

The polymer blend includes: a first phase that is continuous and a second phase that is phase-separated from the first continuous phase. As used herein, "phases" of a polymer blend are intended to refer to domains that include materials (e.g., homopolymers, copolymers, and/or miscible mixtures of polymers) that are substantially homogeneous, and preferably homogeneous, on a microscopic level. More specifically, the term "continuous phase" is intended to refer to a phase in which any point within the phase can be reached by travelling from any other point within the phase without exiting the phase (i.e., the path travelled between the points is entirely within the phase).

Correspondingly, a phase that is "phase-separated" from a continuous phase is intended to refer to a domain that has a physical boundary from the other phase or phases. The phase that is phase-separated can be a discrete phase or another continuous phase. As used herein, "discrete phase" is intended to refer to a phase that includes a plurality of non-connected domains of the same composition. The domains of the discrete phase can be symmetrical (e.g., spherical) or unsymmetrical (e.g., needle shaped). Optionally, unsymmetrical domains of a phase-separated phase can be oriented in one or more directions. In certain embodiments, the phase-separated phase can be anisotropic and oriented along one axis (i.e., uniaxially oriented) to result in domains having an aspect ratio (i.e., the maximum dimension of the phase divided by the minimum dimension of the phase) of at least 1.1. In other embodiments, the phase-separated phase can be oriented in two directions.

The polymer blend typically includes at least 0.1% by weight of the second phase-separated phase, based on the total weight of the polymer blend, and in certain embodiments at least 0.5%, 1%, 2%, 3%, 5%, 10%, 15%, 20%, 25%, 30%, 35%, 40%, 45%, or 50% by weight of the second phase-separated phase, based on the total weight of the polymer blend.

The first continuous phase includes a first biodegradable polymer (e.g., a polylactide homopolymer or copolymer). As used herein, "biodegradable" and "bioerodible" are used interchangeably and are intended to broadly encompass materials including, for example, those that tend to break down upon exposure to physiological environments. In certain embodiments, one or both of the first and second polymers are biodegradable polymers that can optionally biodegrade at sufficiently high rates to enable them to be considered for use in specific medical device applications.

The continuous phase that includes the first biodegradable polymer typically is capable of contributing to the mechanical stability of the device, especially at the upper temperature range at which the device may be made, implanted, and/or used (e.g., 37° C. and above). As such, the continuous phase typically has a glass transition temperature of at least 40° C., and in certain embodiments at least 41° C., 42° C., 43° C., 44° C., 45° C., 46° C., 47° C., 48° C., 49° C., 50° C., 55° C., or 60° C.

In certain embodiments, the first biodegradable polymer having chains included in the continuous phase can, for example, be an amorphous glassy material, which may be rigid and brittle below its glass transition temperature. As used herein, the term "rigid" means that the material has a modulus (E) of greater than 0.5 GPa at the temperature of interest. As used herein, the term "brittle" means that the material has a strain at break (epsilon) of less than 10%.

Although a wide variety of polymers can be used as the first biodegradable polymer, exemplary polymers include, but are not limited to, polylactides (e.g., homopolymers and/or copolymers). Polylactide homopolymers and copolymers include, for example, poly(L-lactide) (PLLA), poly(D,L-lactide) (PDLLA), poly(L-lactide-co-D,L-lactide) (PLDLLA), poly(L-lactide-co-glycolide) (PLGA), poly(D,L-lactide-co-glycolide) (PDLGA), poly(lactide-co-caprolactone), poly(lactide-co-trimethylene carbonate), poly(lactide-co-hydroxybutyrate), poly(lactide-co-dioxane), and combinations thereof.

The chains of the first biodegradable polymer are oriented along an axis. As used herein, "oriented" is intended to refer to a non-isotropic chain orientation in which at least one of the assembly average chain projections at the X, Y, and/or Z directions is different than the remaining projection or projections.

The second phase of the polymer blend is phase-separated from the first continuous phase and is typically more flexible than the first continuous phase, especially at the lower temperature range at which the device may be made, implanted, and/or used (e.g., 25° C. and below). As such, the phase-separated phase typically has a glass transition temperature of 15° C. or less, and in certain embodiments 14° C. or less, 13° C. or less, 12° C. or less, 11° C. or less, 10° C. or less, 5° C. or less, 0° C. or less, −5° C. or less, or −10° C. or less.

In certain embodiments, the second biodegradable polymer included in the second phase-separated phase can, for example, be an amorphous polymer that is rubbery above its glass transition temperature. As used herein, the term "rubbery" means that the material has a modulus (E) of less than 0.5 GPa at the temperature of interest. In certain embodiments, the second biodegradable polymer can, for example, be a rubbery material at room temperature.

Although a wide variety of polymers can be used for the second biodegradable polymer, exemplary polymers include, but are not limited to, poly(trimethylene carbonate) (PTMC), polycaprolactone (PCL), polyhydroxybutyrate, polydioxane, and combinations thereof.

In some embodiments, the modulus of the polymer blend parallel to the axis of orientation is at least 100% of the modulus of the first biodegradable polymer; and the strain at break of the polymer blend parallel to the axis of orientation is at least 120% of the strain at break of the first biodegradable polymer.

in other embodiments, the modulus of the polymer blend parallel to the axis of orientation is at least 90% of the modulus of the first biodegradable polymer, the strain at break of the polymer blend parallel to the axis of orientation is at least 120% of the strain at break of the first biodegradable polymer, and the polymer blend includes at least 5% by weight of the second phase, based on the total weight of the polymer blend.

In other certain embodiments, the modulus of the polymer blend parallel to the axis of orientation is at least 80% of the modulus of the first biodegradable polymer; the strain at break of the polymer blend parallel to the axis of orientation is at least 120% of the strain at break of the first biodegradable polymer; and the polymer blend includes at least 20% by weight of the second phase, based on the total weight of the polymer blend.

The modulus and strain at break of the first biodegradable polymer can be determined by the following method. The well dried biodegradable polymer can be press molded at a suitable temperature for a time effective to form a film. Typically, the thickness of the film is 0.5 mm to 1 mm. Typically, a suitable temperature is a temperature that is high enough to allow the polymer to flow, but not so high as to cause substantial degradation of the polymer over the molding time. Microtensile bars (ASTM D1708) can be cut from the film with a die cutter and tensile-tested.

The modulus and strain at break parallel to the axis of orientation of a polymer blend film that has been stretched, and in certain embodiments quenched, can be determined by the following method. Typically, the thickness of the film is 0.5 mm to 1 mm. Microtensile bars (ASTM D1708) can be cut from the polymer blend film with a die cutter with the long axis of the microtensile bars being aligned parallel to the direction of stretching. The microtensile bars can then be tested according to ASTM D1708.

The modulus of the polymer blend parallel to the axis of orientation is typically at least 80%, 90%, 100%, 110%, or 125% of the modulus of the first biodegradable polymer. The strain at break of the polymer blend parallel to the axis of orientation is typically at least 120%, 130%, 140%, 150%, 200%, 300%, 500%, 1000%, or 2000% of the strain at break of the first biodegradable polymer.

In certain embodiments, the modulus and strain at break of the polymer blend in a direction perpendicular to the axis of orientation can be different than the modulus and strain at break of the polymer blend parallel to the axis of orientation (i.e., the polymer blend exhibits anisotropic properties). In certain embodiments the modulus and strain at break of the polymer blend in at least one direction perpendicular to the axis of orientation can be sufficient for use in an implantable medical device.

The modulus and strain at break perpendicular to the axis of orientation of a polymer blend film that has been stretched, and in certain embodiments quenched, can be determined by the following method. Typically, the thickness of the film is 0.5 mm to 1 mm. Microtensile bars (ASTM D1708) can be cut from the polymer blend film with a die cutter with the long axis of the microtensile bars being aligned perpendicular to the direction of stretching. The microtensile bars can then be tested according to ASTM D1708.

The modulus of the polymer blend in a direction perpendicular to the axis of orientation is typically at least 75%, 80%, 85%, 90%, 95%, or 100% of the modulus of the first biodegradable polymer. The strain at break of the polymer blend in a direction perpendicular to the axis of orientation is typically at least 100%, 200%, 300%, 500%, 1000%, or 2000% of the strain at break of the first biodegradable polymer.

In addition to the first and second biodegradable polymers, polymer blends as described herein can include other additional components including, but not limited to, compatibilizers (e.g., copolymers), plasticizers, bonding promoters, and combinations thereof.

In another aspect, the present disclosure provides a method of preparing an implantable medical device. The method includes: blending (e.g., melt blending) components including a first biodegradable polymer having chains and a second biodegradable polymer under conditions effective to form a polymer blend. The polymer blend includes: a first phase that is continuous and a second phase that is phase-separated from the first continuous phase. The first continuous phase has a glass transition temperature of at least 40° C. and includes the first biodegradable polymer. The second phase has a glass transition temperature of 15° C. or less and includes the second biodegradable polymer. The method further includes stretching (e.g., melt stretching) the polymer blend under conditions effective to orient the chains of the first biodegradable polymer along the axis of stretching; optionally quenching the stretched polymer blend; and forming a medical device from the stretched and optionally quenched polymer blend.

In some embodiments, the modulus of the stretched and optionally quenched polymer blend parallel to the axis of stretching is at least 100% of the modulus of the first biodegradable polymer; and the strain at break of the stretched and optionally quenched polymer blend parallel to the axis of stretching is at least 120% of the strain at break of the first biodegradable polymer.

In other embodiments, the modulus of the stretched and optionally quenched polymer blend parallel to the axis of stretching is at least 90% of the modulus of the first biodegradable polymer; the strain at break of the stretched and optionally quenched polymer blend parallel to the axis of stretching is at least 120% of the strain at break of the first biodegradable polymer; and the polymer blend includes at least 5% by weight of the second phase, based on the total weight of the polymer blend.

In other certain embodiments, the modulus of the stretched and optionally quenched polymer blend parallel to the axis of stretching is at least 80% of the modulus of the first biodegradable polymer; the strain at break of the stretched and optionally quenched polymer blend parallel to the axis of stretching is at least 120% of the strain at break of the first biodegradable polymer; and the polymer blend includes at least 20% by weight of the second phase, based on the total weight of the polymer blend.

In addition to the first and second biodegradable polymers, one or more of the components that are melt blended can include, for example, one or more of a wide variety of additives, and particularly particulate additives, such as, for example, fillers (e.g., including particulate, fiber, and/or platelet material), other polymers (e.g., polymer particulate materials such as polytetrafluoroethylene can result in higher modulus), imaging particulate materials (e.g., barium sulfate for visualizing material placement using, for example, fluoroscopy), biologically derived materials (e.g., bone particles, cartilage, demineralized bone matrix, platelet gel, and combinations thereof), and combinations thereof. Other additives include, but are not limited to, biologically active agents, wetting agents for improving wettability to hydrophobic surfaces, antioxidants to improve oxidative stability, dyes or pigments to impart color or radiopacity, plasticizers, solvents, stabilizers, compatibilizers (e.g., copolymers), and bonding promoters. Additives can be dissolved, suspended, and/or dispersed within the blend. For particulate additives, the additive is typically dispersed within the blend.

The components including the first biodegradable polymer and the second biodegradable polymer (as described herein) are blended under conditions effective to form a continuous phase including the first biodegradable polymer and a phase-separated-phase including the second biodegradable polymer. A wide variety of blending methods can be used including, for example, melt blending, solvent blending, dry powder mixing, solid state shear pulverization, and/or blending in supercritical carbon dioxide.

As used herein, the term "melt blending" is meant to include mixing at temperatures at which at least one component is melted and can flow under stress. Melt blending can be carried out using a wide variety of methods including, for example, dispersing and/or distributing. Mixing can be carried out using, for example, a simple shear machine, a Banbury mixer, a single or twin screw extruder, a helicone mixer, a multidirectional rotation mixer, or combinations thereof.

Specific melt blending conditions effective to form a continuous phase including the first biodegradable polymer and a phase-separated-phase including the second biodegradable polymer will vary depending on the specific combination of biodegradable polymers selected for blending. However, effective melt blending conditions will be apparent to one of skill in the art in view of the description and examples included in the present disclosure, in addition to melt blending conditions known in the art. See, for example, *Polymer Alloys and Blends: Thermodynanics and Rheology*, Utracki, Ed., Hanser Publishers, New York (1990).

For certain embodiments, the first component includes one or more polylactide homopolymers and/or copolymers, and the second component includes one or more of poly(trimethylene carbonate) (PTMC), polycaprolactone (PCL), polyhydroxybutyrate, and polydioxane. For such certain embodiments, melt blending conditions effective to form a continuous phase including the one or more polylactide homopolymers and/or copolymers, and a phase-separated phase including the one or more of poly(trimethylene carbonate) (PTMC), polycaprolactone (PCL), polyhydroxybutyrate, and polydioxane, typically include a temperature of 60° C. to 250° C. (and in certain embodiments 60° C. to 230° C.), a mixing rate of 10 revolutions per minute (rpm) to 300 rpm (depending on the mixing device), for a time of 1 minute to 1 hour.

In some embodiments, the conditions used for melt blending the first biodegradable polymer and the second biodegradable polymer can be effective to result in reactive blending. As used herein, the term "reactive blending" is used to refer to a method in which one or more new components are generated during mixing. For example, reactive blending of poly(m-ethyl methacrylate) and bisphenol A polycarbonate can result in the formation of copolymers.

In certain embodiments, the conditions used for melt blending PLGA and PTMC can be effective to result in a trans-esterification reaction that results in chain segment exchange between ester groups of the PLGA and carbonate groups of the PTMC. Chain segment exchange can result in the formation of block copolymers PLGA:PTMC. Because the reaction may occur randomly within chains, the resulting copolymers may be random multiple block copolymers. The in situ formation of such copolymers can be advantageous in that potentially difficult and/or expensive methods of separately preparing such copolymers (e.g., as compatibilizers) can potentially be avoided.

For embodiments in which the conditions used for melt blending the first biodegradable polymer and the second biodegradable polymer are effective to form a copolymer having segments of the first polymer and segments of the second polymer, the copolymer can have a preference for location at an interface between the domain including the first polymer and the domain including the second polymer. Because such copolymers can have a preference for location at an interface between domains, the copolymer can act in a manner similar to a surfactant, for example, to increase interfacial bond strength between domains and/or to reduce dispersed domain size, effects which can improve toughness of the blend.

The components including the first biodegradable polymer and the second biodegradable polymer (as described herein) can also be blended by solvent blending. Solvent blending typically includes dissolving or dispersing each polymer in a solvent, then removing the solvent from the solution or dispersion of the polymers. Typically the same solvent is used to dissolve or disperse each polymer to be blended. Alternatively, different solvents may be used to dissolve or disperse each polymer. Typically, each solvent is at least partially soluble in the other solvent. Typically, solutions or dispersions include 0.1% to 99.9% by weight of each polymer. A wide variety of solvents can be used including, for example, tetrahydrofuran (THF), chloroform, methylene chloride, and combinations thereof. Preferably the solvents have sufficient volatility to allow for removal under reduced pressure.

The components including the first biodegradable polymer and the second biodegradable polymer (as described herein) can also be blended using supercritical carbon dioxide.

The polymer blend having a continuous phase and a phase-separated phase (as described herein) can be stretched under conditions effective to orient the chains of the first biodegradable polymer along the axis of stretching. Stretching can include one or more of melt stretching, cold stretching, and combinations thereof. As used herein, the term "melt stretching" is meant to include stretching a material at a temperature at or above the Tg of the material. As used herein, the term "cold stretching" is meant to include stretching a material at a temperature lower than the Tg of the material. Stretching can be simultaneous with and/or subsequent to blending.

Stretching can be carried out using a wide variety of methods including, for example, uniaxial drawing, biaxial drawing, extrusion, injection molding, blow molding, blowing film, and combinations thereof. Stretching conditions effective to orient the chains of the first biodegradable polymer along the axis of stretching typically include a stretching ratio of greater than 1 to 100, wherein the stretching ratio is defined as the length along an axis of stretching after stretching divided by the length along the same axis before stretching. Stretching can conveniently be reported as stretching (%), which is equal to 100 times the (stretching ratio −1). Stretching is carried out at a rate selected to avoid breaking the sample. Typically the stretching rate (stretching ratio per unit time) is at most 20 per minute, in some embodiments at most 10 per minute, and in certain embodiments at most 5 per minute. In certain embodiments, the stretching is carried out at a temperature that is at or above the Tg of at least one of the biodegradable polymers. Typically, stretching is carried out at a temperature of room temperature (e.g., 25° C.) or above. In some embodiments stretching is carried out at a temperature of no greater than 180° C., in certain embodiments at a temperature of no greater than 150° C., and in some embodiments at a temperature of no greater than 100° C.

Optionally, the stretched polymer blend can be quenched. As used herein, the term "quenching" is meant to include cooling the sample to a temperature at which chain orientation becomes locked or frozen. In certain embodiments, quenching can assist in retention of the orientation along the axis of stretching of the chains of the first biodegradable polymer. Quenching can be carried out using a wide variety of methods including, for example, contact with fluids (gases or liquids), contact with solids, immersion in liquids, and combinations thereof.

Quenching conditions effective to retain the orientation along the axis of stretching of the chains of the first biodegradable polymer typically include a cooling rate high enough such that the degree of chain orientation does not substantially decrease due to relaxation. Typical cooling rates include rates of 50° C./minute to 100° C./second.

For certain embodiments, the first component includes one or more polylactide homopolymers and/or copolymers, and the second component includes one or more of poly(trimethylene carbonate) (PTMC), polycaprolactone (PCL), polyhydroxybutyrate, and polydioxane. For such certain embodiments, melt stretching conditions effective to orient the discrete phase along the axis of stretching typically include a stretching ratio of 1.5 to 5, wherein the stretching ratio is defined as the length along an axis of stretching after stretching divided by the length along the same axis before stretching. Stretching can conveniently be reported as stretching (%), which is equal to 100 times the (stretching ratio −1). Stretching is carried out at a rate selected to avoid breaking the sample. Typically the stretching rate (stretching ratio per unit time) is 1.1 per minute to 10 per minute. In certain embodiments, the stretching is carried out at a temperature that is at or above the Tg of at least one of the biodegradable polymers. Typically, stretching is carried out at a temperature of 60° C. to 100° C. For such certain embodiments, quenching conditions effective to retain at least a portion of the orientation of the discrete phase typically include cooling rates of 10° C./second to 100° C./second.

In certain embodiments, stretched and optionally quenched polymer blends (as described herein) can form a medical device without further processing. For example, the stretched and optionally quenched polymer blends, as prepared, can be in the form of a stent. Alternatively, additional processing steps may optionally be used to form a medical device. For example, the stretched and optionally quenched polymer blend can be extruded or blow molded to form medical devices such as, for example, stents.

In certain embodiments, the stretched and optionally quenched polymer blends (as disclosed herein) can be shaped to form a medical device, preferably a biodegradable medical device. The stretched and optionally quenched polymer blends can be shaped by methods known in the art including compression molding, injection molding, casting, extruding, milling, blow molding, or combinations thereof. As used herein, a "medical device" includes devices that have surfaces that contact tissue, bone, blood, or other bodily fluids in the course of their operation, which fluids are subsequently used in patients. This can include, for example, extracorporeal devices for use in surgery such as blood oxygenators, blood pumps, blood sensors, tubing used to carry blood, and the like which contact blood which is then returned to the patient. This can also include endoprostheses implanted in blood contact in a human or animal body such as vascular grafts, stents, pacemaker leads, heart valves, and the like, that are implanted in blood vessels or in the heart. This can also include devices for temporary intravascular use such as catheters, guide wires, and the like which are placed into the blood vessels or the heart for purposes of monitoring or repair.

In some embodiments, stretched and optionally quenched polymer blends (as described herein) have physical properties (e.g., mechanical properties) that are useful for certain medical devices.

The present invention is illustrated by the following examples. It is to be understood that the particular examples, materials, amounts, and procedures are to be interpreted broadly in accordance with the scope and spirit of the invention as set forth herein.

EXAMPLES

MATERIALS: All parts, percentages, ratios, and the like in the examples are by weight, unless noted otherwise. $M_n$ represents number average molecular weight, and $M_w$ represents weight average molecular weight. Unless otherwise noted, all solvents and reagents were or can be obtained from Sigma-Aldrich Corp., St. Louis, Mo.

Poly(L-lactide-co-glycolide) (PLGA; lactic acid:glycolic acid molar ratio of 85:15; intrinsic viscosity of 5 to 7) was obtained from Boehringer Ingelheim (Ingelheim, Germany) under the trade designation RESOMER LG 857. Poly(L-lactide-co-D,L-lactide) (PLDLLA; L-lactide:D,L-lactide molar ratio of 70:30; intrinsic viscosity of 5.5 to 6.5) was obtained from Boehringer Ingelheim (Ingelheim, Germany) under the trade designation RESOMER LR 708. Poly(L-lactide-co-ϵ-caprolactone) (PLC; L-lactide:ϵ-caprolactone molar ratio of 70:30; intrinsic viscosity of 1.2 to 1.8) was obtained from Boehringer Ingelheim (Ingelheim, Germany) under the trade designation RESOMER LC 703. Polycaprolactone (PCL; CAS Number 24980-41-4; Average $M_n$ of 80,000) was obtained from Sigma-Aldrich (St. Louis, Mo.) as Product No. 440744. Poly(trimethylene carbonate) (PTMC; Average $M_w$ of 200-300; polydispersity index (PDI) of 1.5) was prepared by methods similar to those disclosed in Zhang et al., *Biomaterials*, 26:2089-2094 (2005).

PREPARATION OF BLENDS: Small scale PLGA:PTMC blends (nominally 50 cm$^3$) were made with a Haake PolyLab batch mixer available from Thermo Scientific (Walther, Mass.) under the trade designation RHEOMIX 600P and equipped with Brabender type blades. The blends were used to study mechanical and degradation properties. Dry components were premixed at 57° C. for 18 hours with a desiccant dryer. The premix was fed into the mixer and the premix was melt mixed at 180° C. to 215° C. with a blade rotation rate of 50 to 100 revolutions per minute (rpm) for 7 to 8 minutes. Samples were taken from the mixer and allowed to ambiently cool in sealed containers to avoid exposure to moisture.

Larger scale PLGA:PTMC blends (greater than 3 Kg) were made with a Haake PolyLab twin screw extruder available from Thermo Scientific (Walther, MA) under the trade designation RHEOMEX PTW 25. The screw diameter (D) was 25 mm and the screw length/barrel diameter (L/D ratio) was 40.

TEST PROCEDURES: The blend samples were compressed into sheets using a hot press (Wabasa, USA). Samples (20 grams) were placed between two polytetrafluoroethylene films on a square metal frame (15 cm×15 cm×0.1 cm) and transferred to a preheated hot press (225° C.) and warmed for 2 minutes. A compression force (equivalent to 7 MPa pressure) was then applied for 2 more minutes, the force was released, and the samples were quenched to room temperature with a press to provide sheets.

The sheets were cut into rectangular pieces (5 cm×3.8 cm). Some samples were used directly for mechanical testing of unstretched samples. Other samples were loaded in a tensile testing instrument (MTS, MN). The grips and samples were housed with a heating chamber and heated for 10 minutes to reach equilibrium at 75° C. The gage length between the two grips was set at 2.5 cm and loaded samples were stretched at a rate of 25.4 cm/min to the desired stretching ratio. The samples were then immediately quenched by immersion in water or by contact with water soaked paper to provide the stretched and quenched samples.

Micro-tensile bars (ASTM D1708) were cut from the stretched and quenched sheets with a die cutter at directions both parallel and perpendicular to the stretching direction. Tensile tests were performed at room temperature at a cross head rate of 2.54 cm/min with an MTS tensile instrument. Yielding points were determined as 2% strain after the maximum modulus.

Morphologies of microstructures of blend samples were evaluated with both scanning electron microscopy (SEM, Jeol 5900) and transmission electron microscopy (TEM, Jeol 1210). For scanning electron microscopy, morphologies were determined from fracture surfaces of samples. Fracturing was conducted in liquid nitrogen to prevent shear deformation. The sample surface was coated with a 5 nm layer of gold to prevent static. For transmission electron microscopy, samples were microtomed into 50 nm thick slices (Leica). The slices were stained with $RuO_4$ vapor by hanging the slices above a 0.5 wt % $RuO_4$ aqueous solution in a closed bottle for 20 minutes.

Chain orientation was evaluated with X-ray scattering tests. A Bruker-AXS Microdiffractometer with a beam collimator of 0.8 mm, and a sample to detector distance of 15.1 cm was used for the evaluation. Data were acquired using an area detector, with a two-theta range of 30°, centered at two-theta values of 0° and 30°, and exposure times of 60 seconds.

Thermal transition properties of samples were evaluated using differential scanning calorimetry (DSC) (Pyris 1, PekinElmer). Samples were typically scanned twice at 40° C./minute. The second scans were used to improve the signal to noise ratio.

Material degradation tests were performed with disc samples (12.5 mm diameter and 0.75 mm thick) that were cut from hot-pressed films. Individual discs were immersed in phosphate buffered aqueous solution (PBS, pH 7.4) at 37° C. The volume ratio of testing solution to solid sample was at least 50. The PBS solution was refreshed weekly to monthly to ensure that the pH (7) values of the solutions remained unchanged during the testing. Samples were taken from solutions at desired times for molecular weight measurement using gel permeation chromatography (GPC) (Agilent 1100 unit equipped with Phenogel 5 micron columns) using tetrahydrofuran (THF) as the mobile phase. Absolute molecular weight was obtained for all the samples based on the coupled light scattering (measured at 18 angles with Dawn EOS, Wyatt) and refractive index detection (Optilab DSP, Wyatt).

TESTING RESULTS: The mechanical properties of unstretched samples with PTMC content varying between 0 wt % and 40 wt % were measured, and Young's modulus for each sample was calculated. FIG. 1 shows Young's modulus (GPa; left y-axis, solid squares) and strain at break (%; right y-axis, open squares) for PLGA and each PLGA:PTMC blend as a function of the weight fraction PTMC (x-axis). The error bars represent standard deviation calculated from 3 replicate measurements. The increase in strain at break from 5% for PLGA to near 250% with increasing PTMC loading indicates a substantial increase in toughness for the blends. However, as toughness increased, a corresponding decrease in Young's modulus was observed.

Figure 2A:
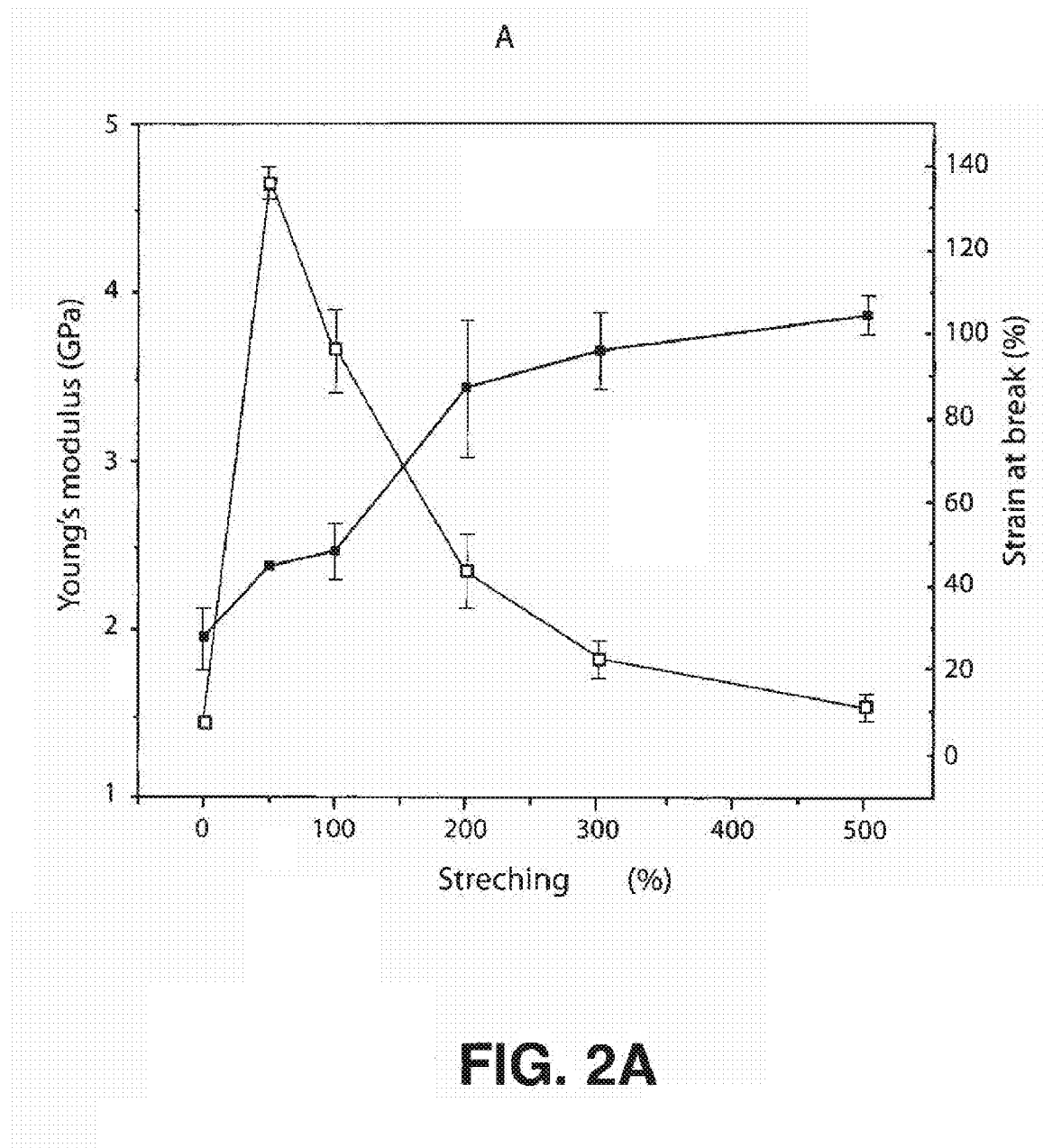
FIG. 2A is for PLGA.
Figure 2B:
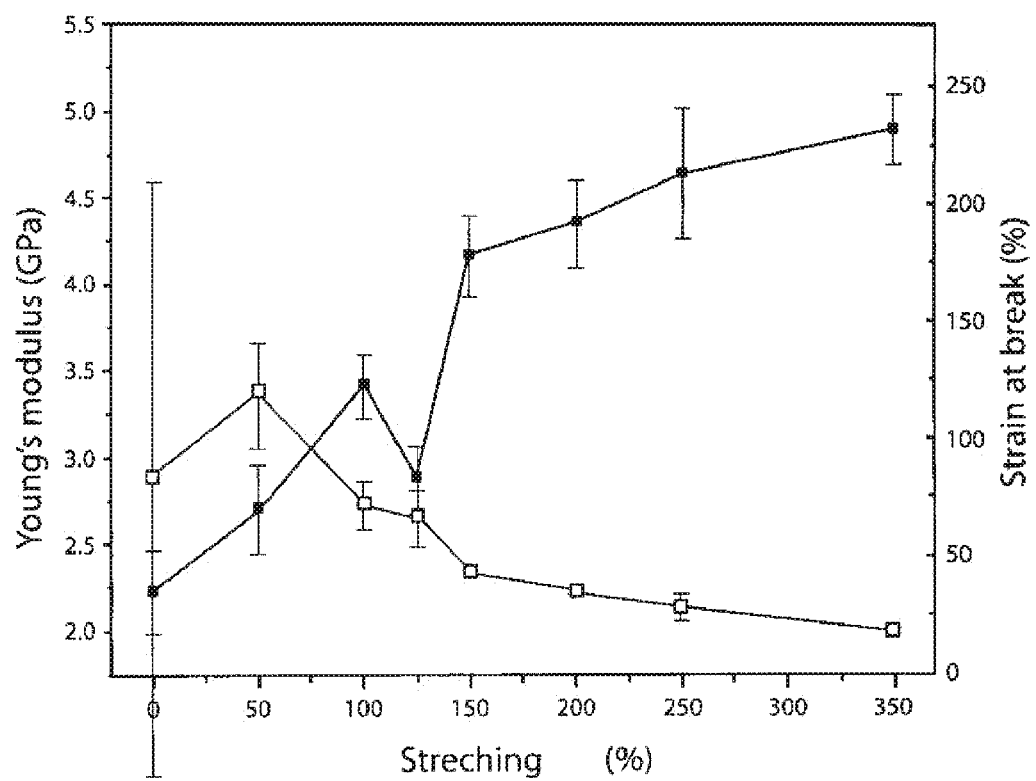
FIGS. 2B-2H are for PLGA:PTMC blends having PTMC contents of 5 wt %, 10 wt %, 15 wt %, 20 wt %, 25 wt %, 30 wt %, and 40 wt %, respectively.
Figure 2C:
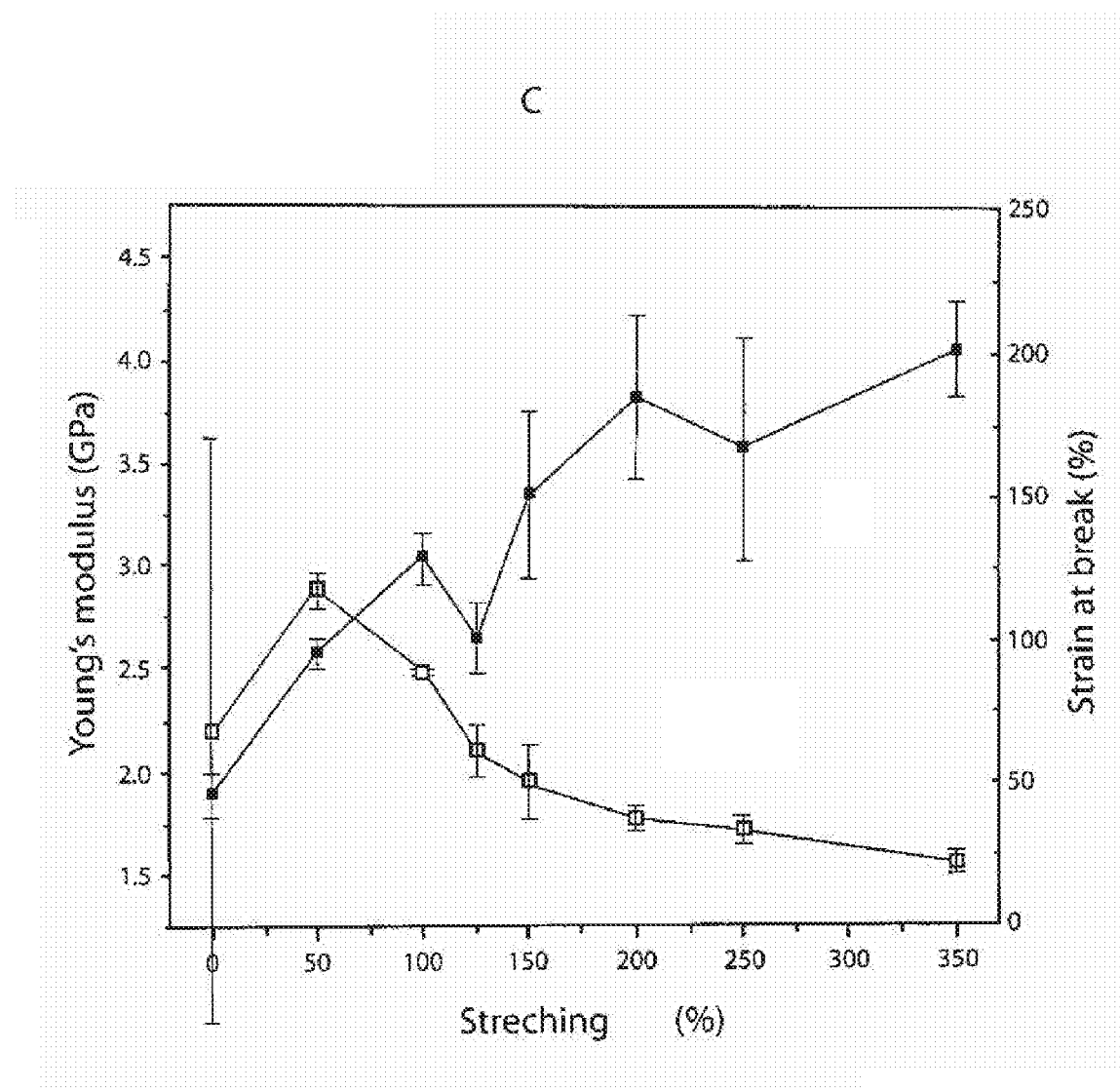
Figure 2D:
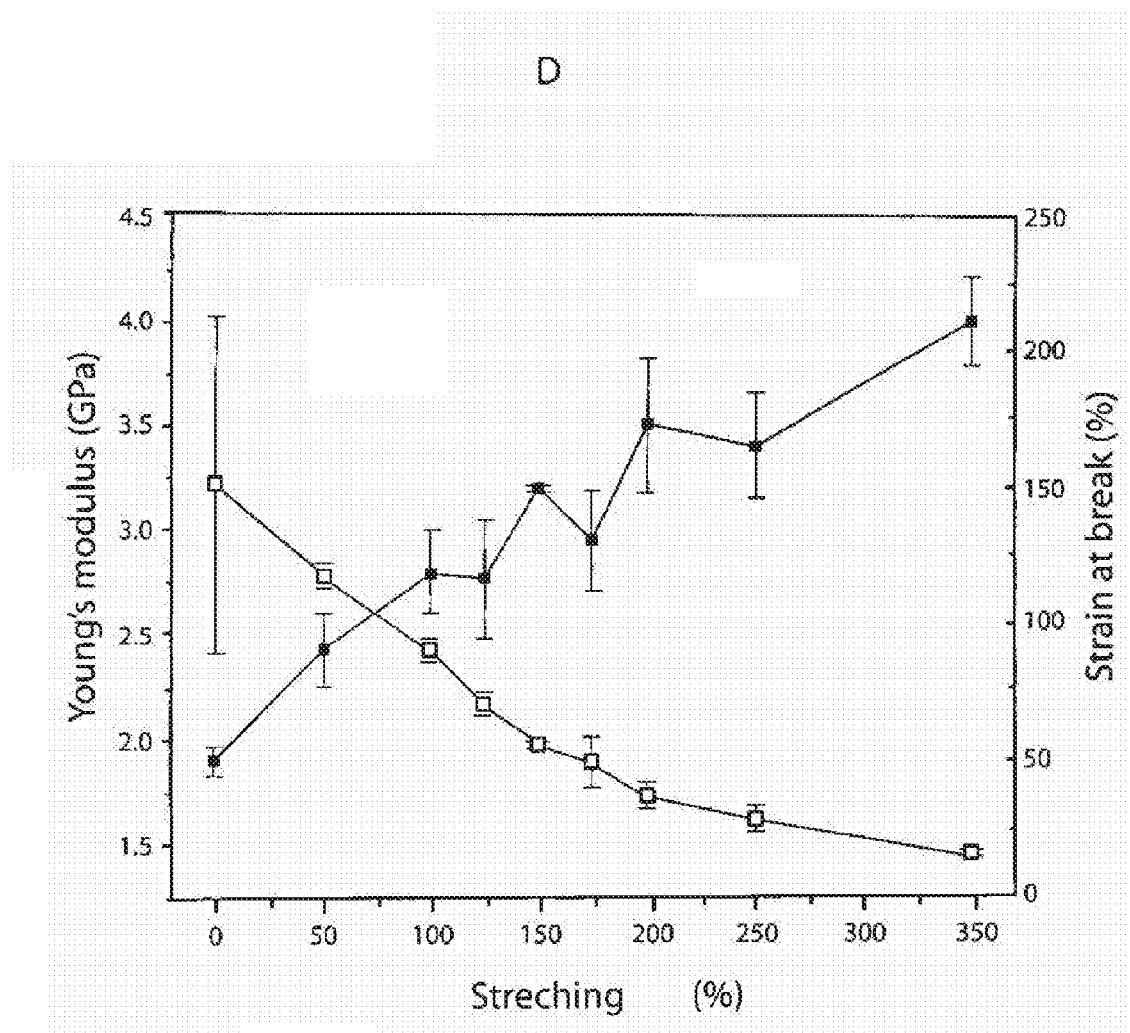
Figure 2E:
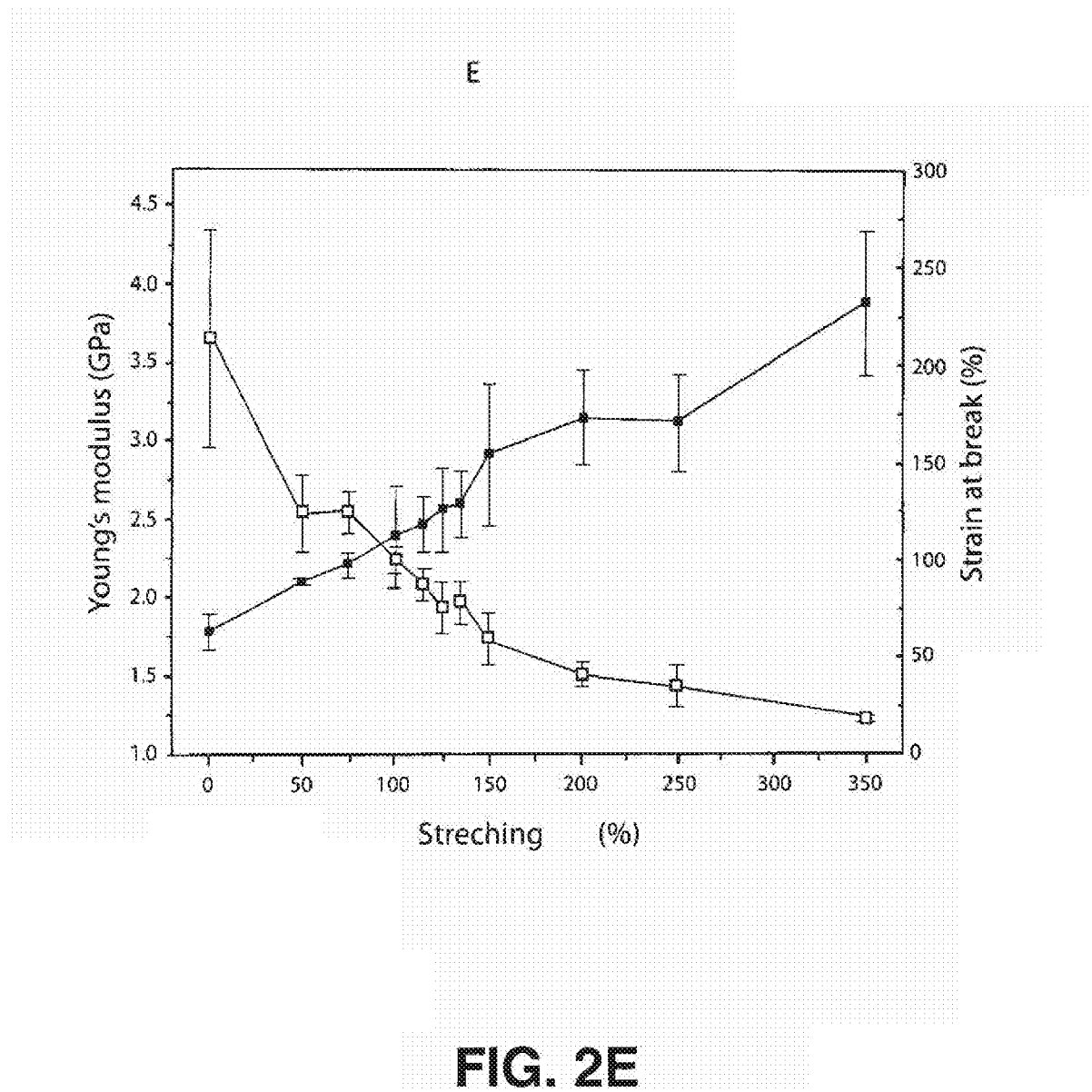
Figure 2F:
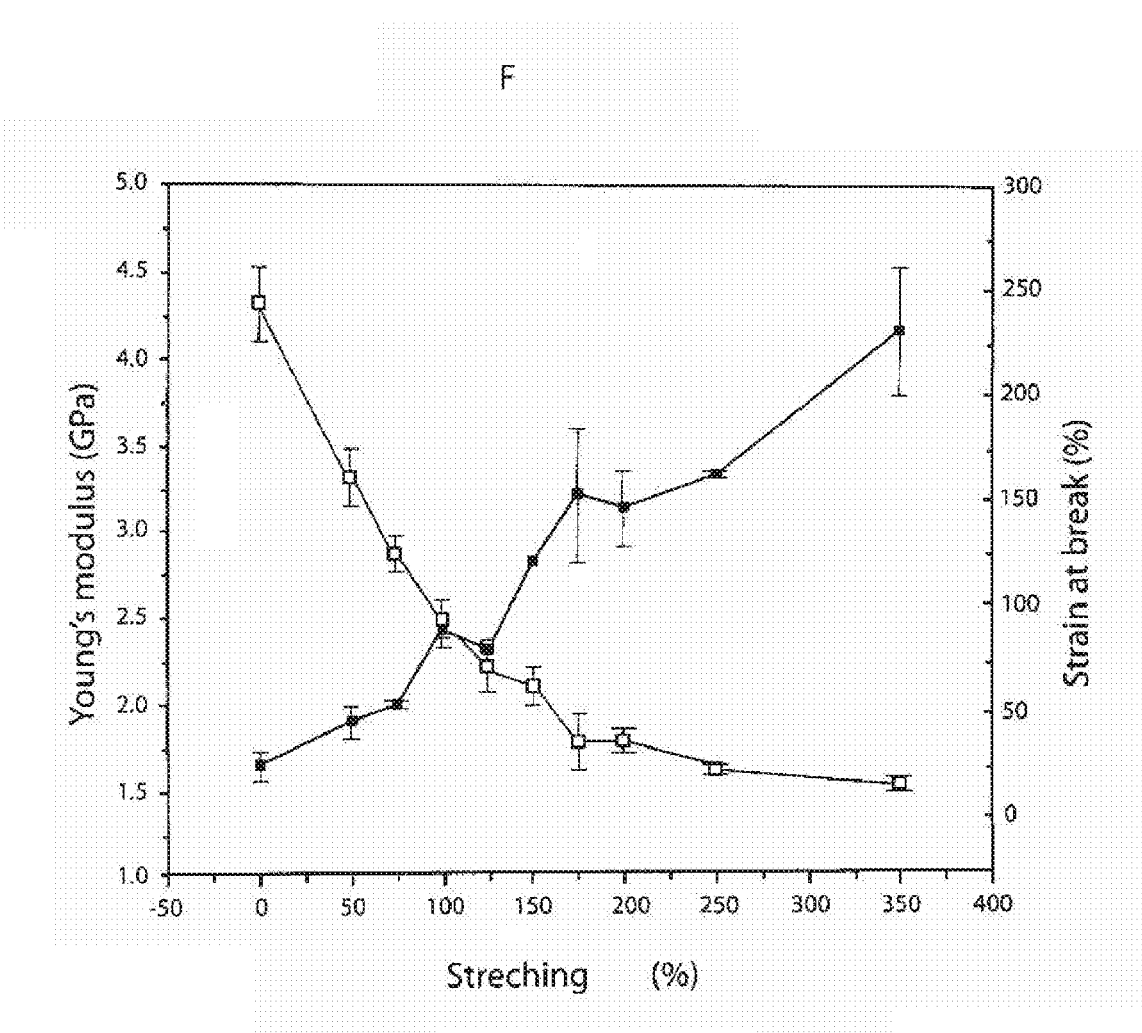
Figure 2G:
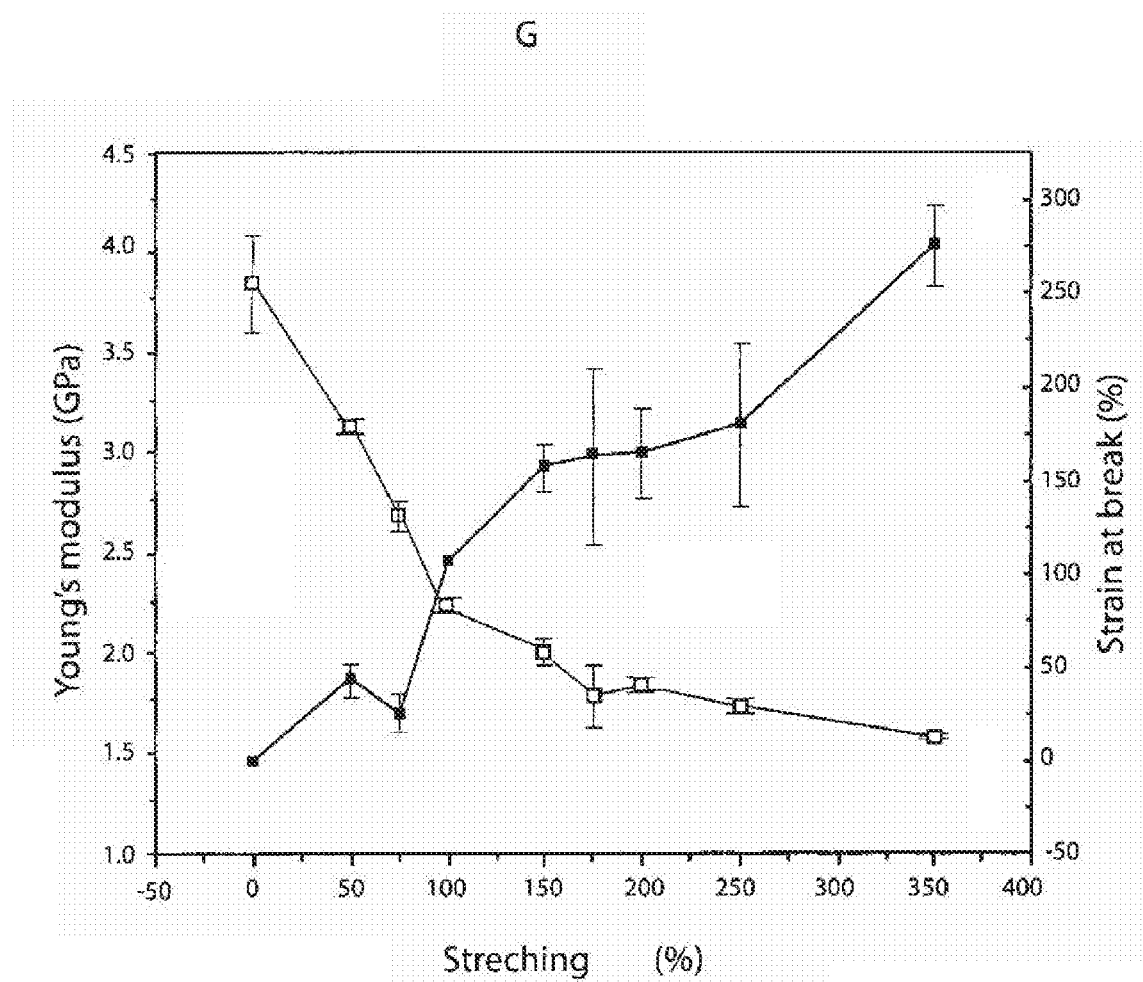
Figure 2H:
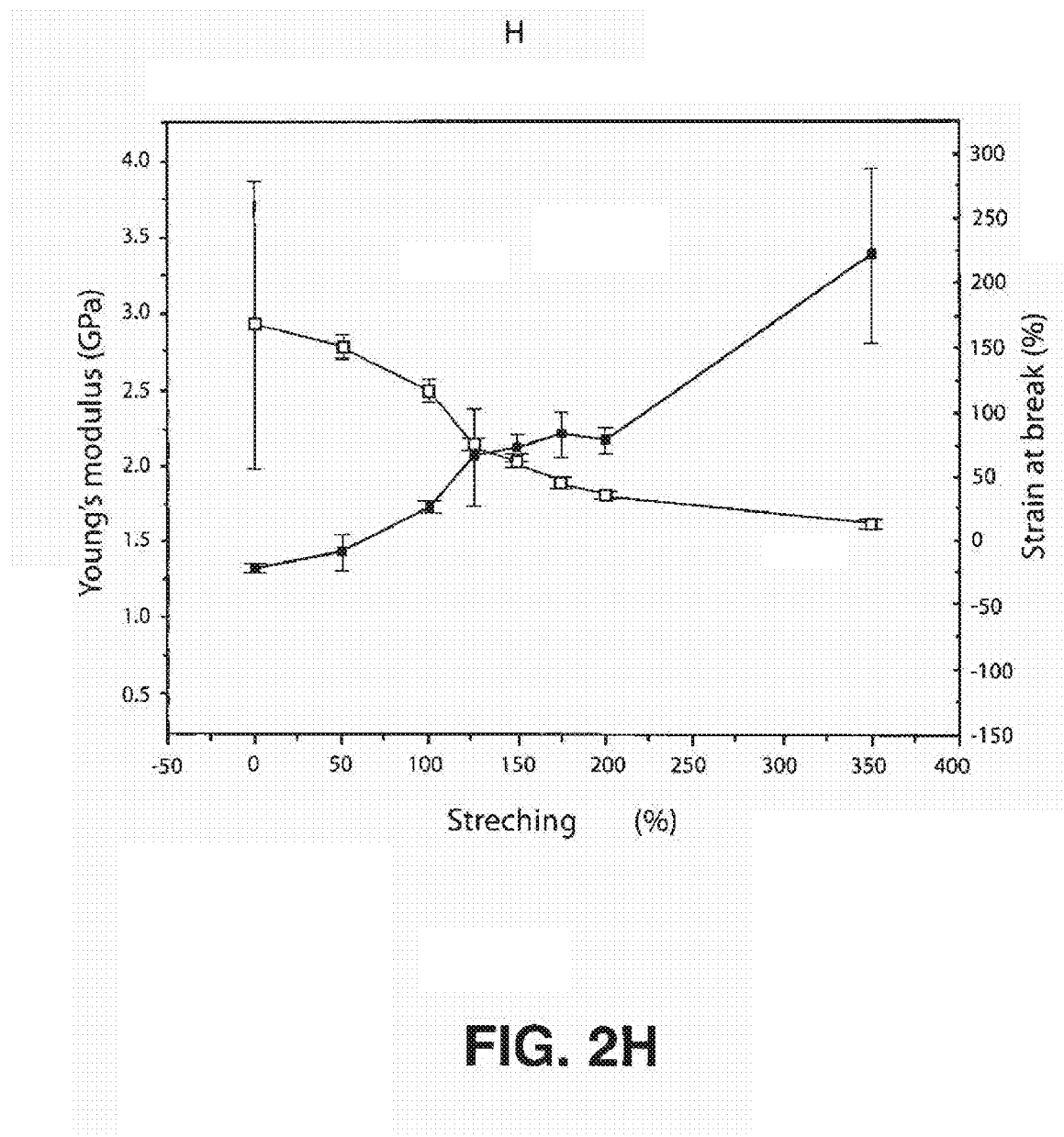

Blends were compressed into sheets and stretched with MTS tensile instrument at a rate of 25.4 cm/min and 75° C. After stretching, the samples were quenched to room temperature immediately with ice water (using wet paper soaked with ice water). Mechanical properties were evaluated by tensile testing at directions both parallel and perpendicular to the stretching directions. FIG. 2 includes graphical representations of Young's modulus (GPa; left y-axis, solid squares) and strain at break (%; right y-axis, open squares) for PLGA and PLGA:PTMC blends at various stretching (%) values parallel to stretching direction. FIG. 2A is for PLGA. FIGS. 2B-2H are for PLGA:PTMC blends having PTMC contents of 5 wt %, 10 wt %, 15 wt %, 20 wt %, 25 wt %, 30 wt %, and 40 wt %, respectively. The error bars represent standard deviation calculated from 3 replicate measurements. All the blends became increasingly rigid at the stretching direction as the stretching (%) was increased. Further, as the stretching (%) was increased, strain at break decreased. However, there is a broad range of PTMC contents and stretching (%) values in which both the modulus and strain at break parallel to the stretching direction were much higher than that of the unstretched pure PLGA (2.3 GPa modulus and 5% strain at break).

Figure 3:
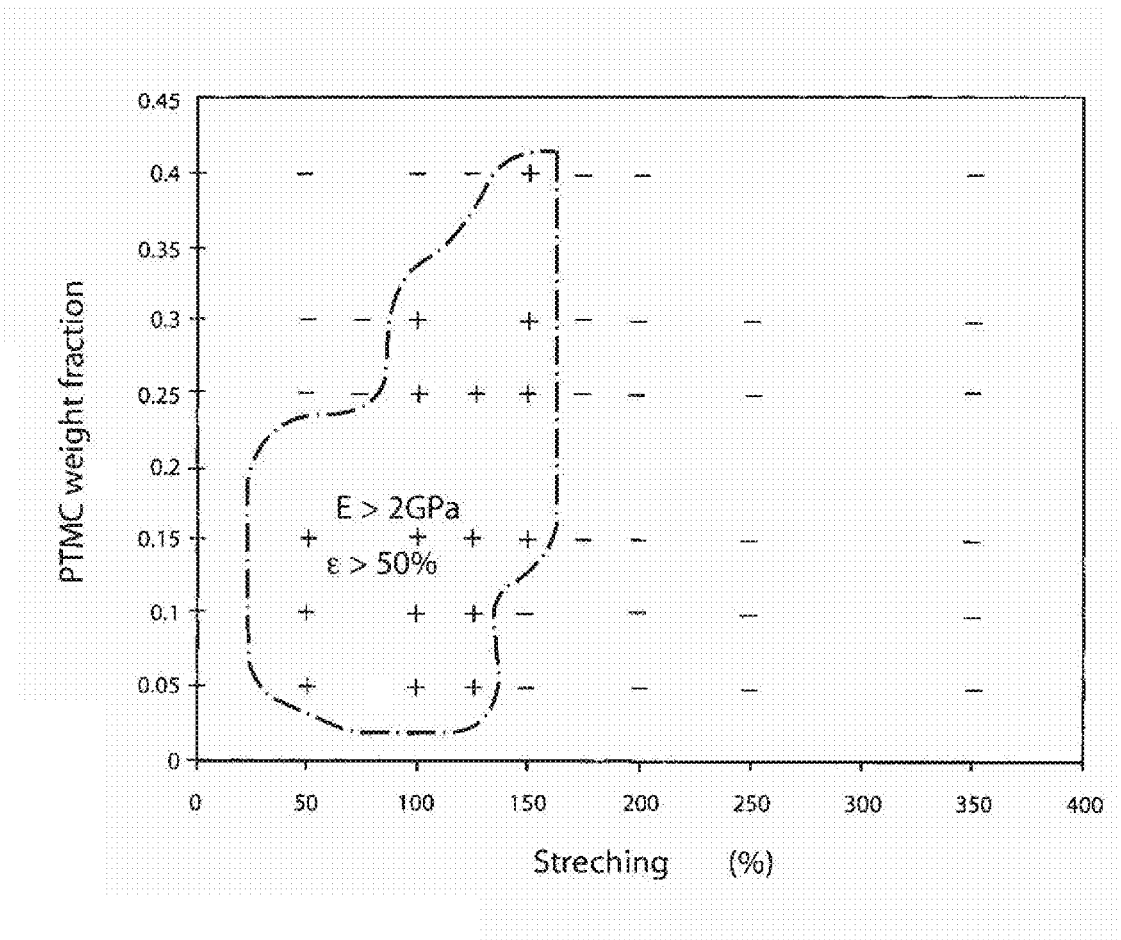
FIG. 3 is a graphical representation mapping toughening and reinforcement observed for PLGA:PTMC blends with various weight fractions of PTMC (y-axis) at various stretching (%) values (x-axis). The area enclosed within the loop represents blends that have Young's modulus greater than 2 GPa and strain at break greater than 50% parallel to stretching direction. The area outside the loop represents blends that have Young's modulus less than 2 GPa and/or strain at break less than 50% parallel to stretching direction.
Figure 4A:
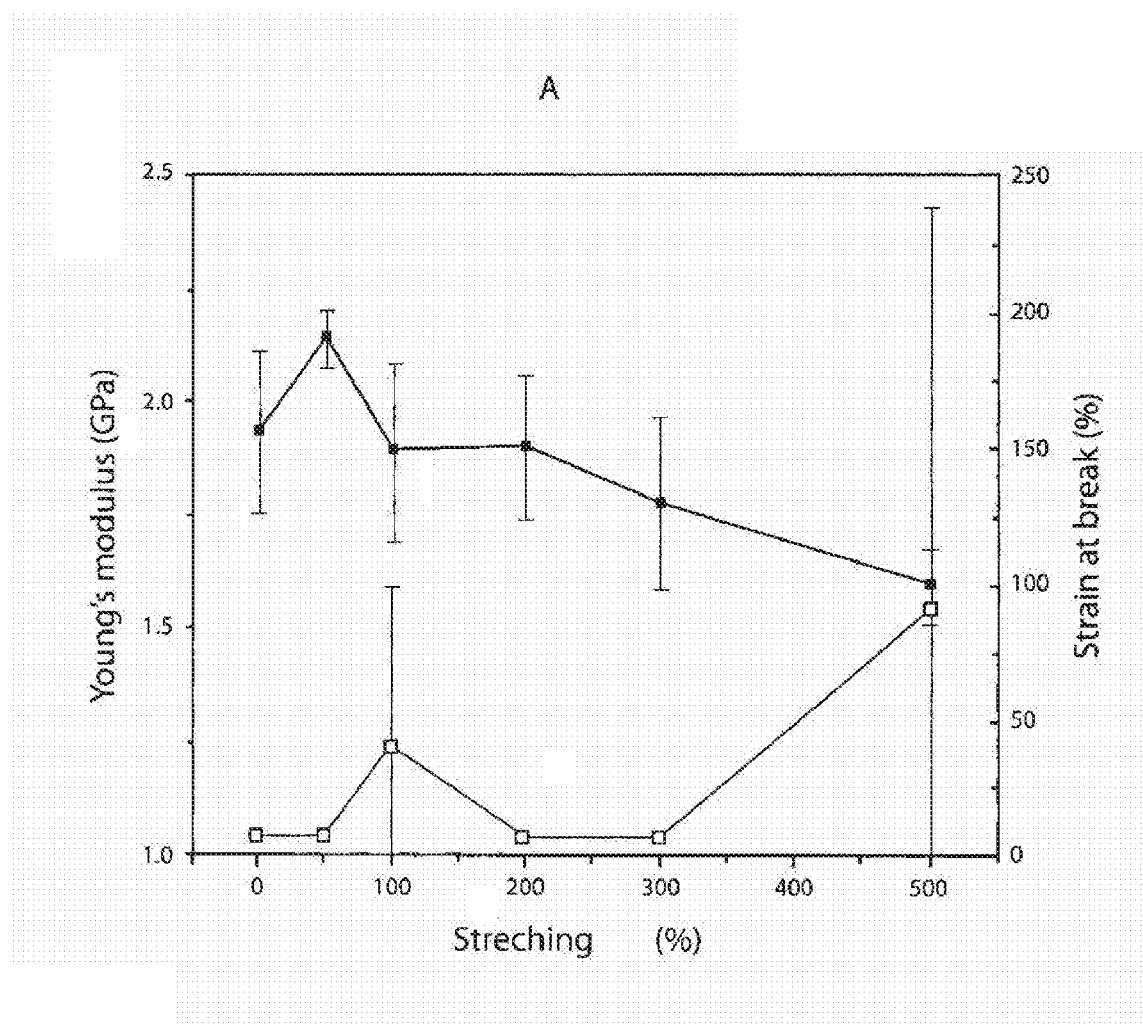
FIG. 4A is for PLGA.
Figure 4B:
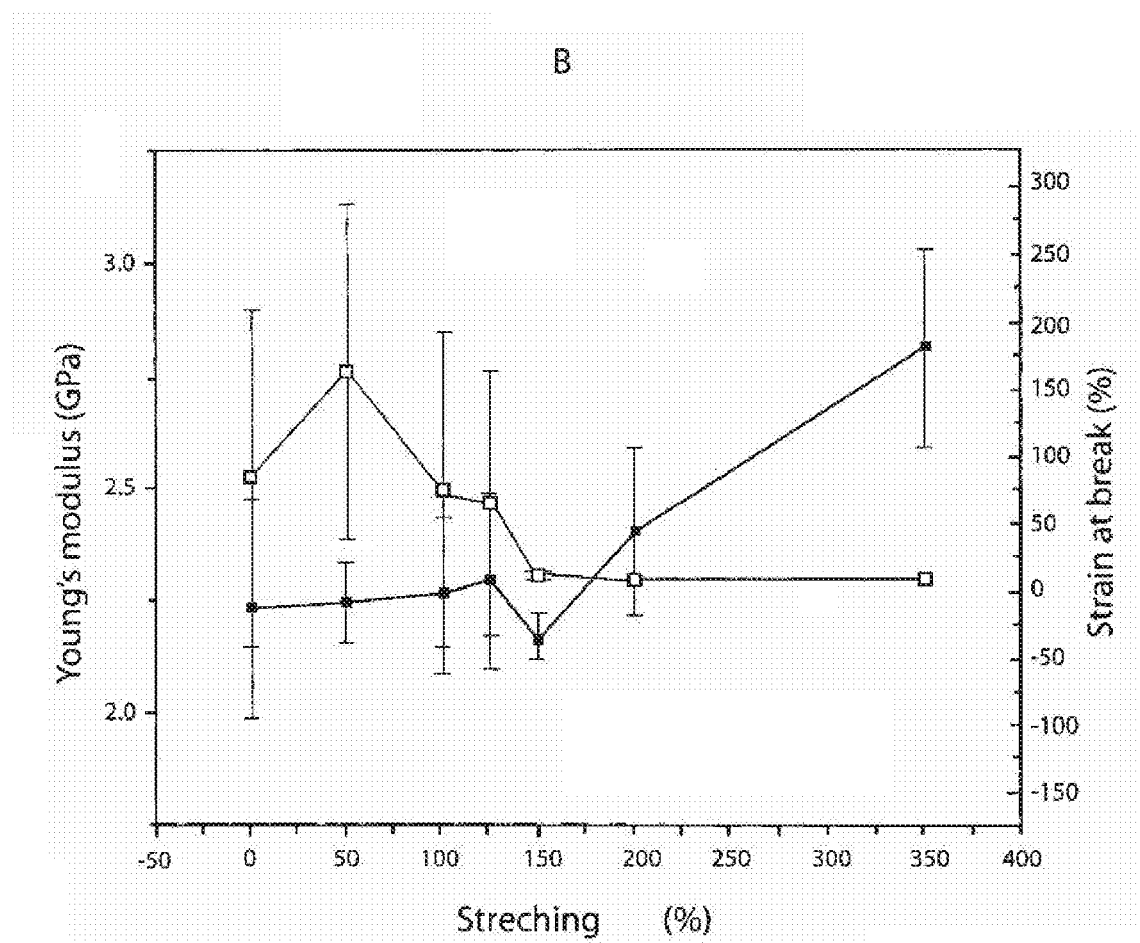
FIGS. 4B-4H are for PLGA:PTMC blends having PTMC contents of 5 wt %, 10 wt %, 15 wt %, 20 wt %, 25 wt %, 30 wt %, and 40 wt %, respectively.
Figure 4C:
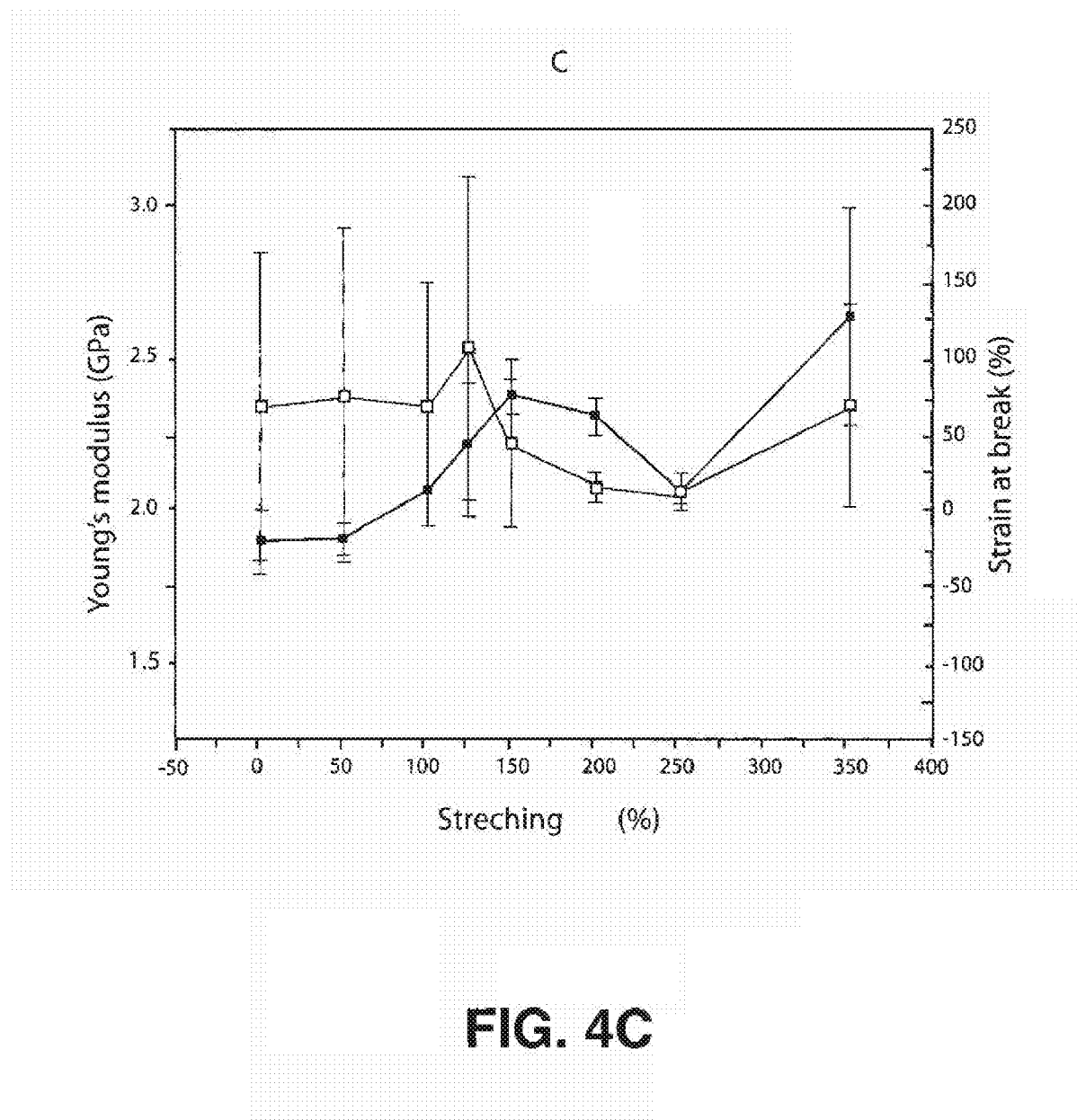
Figure 4D:
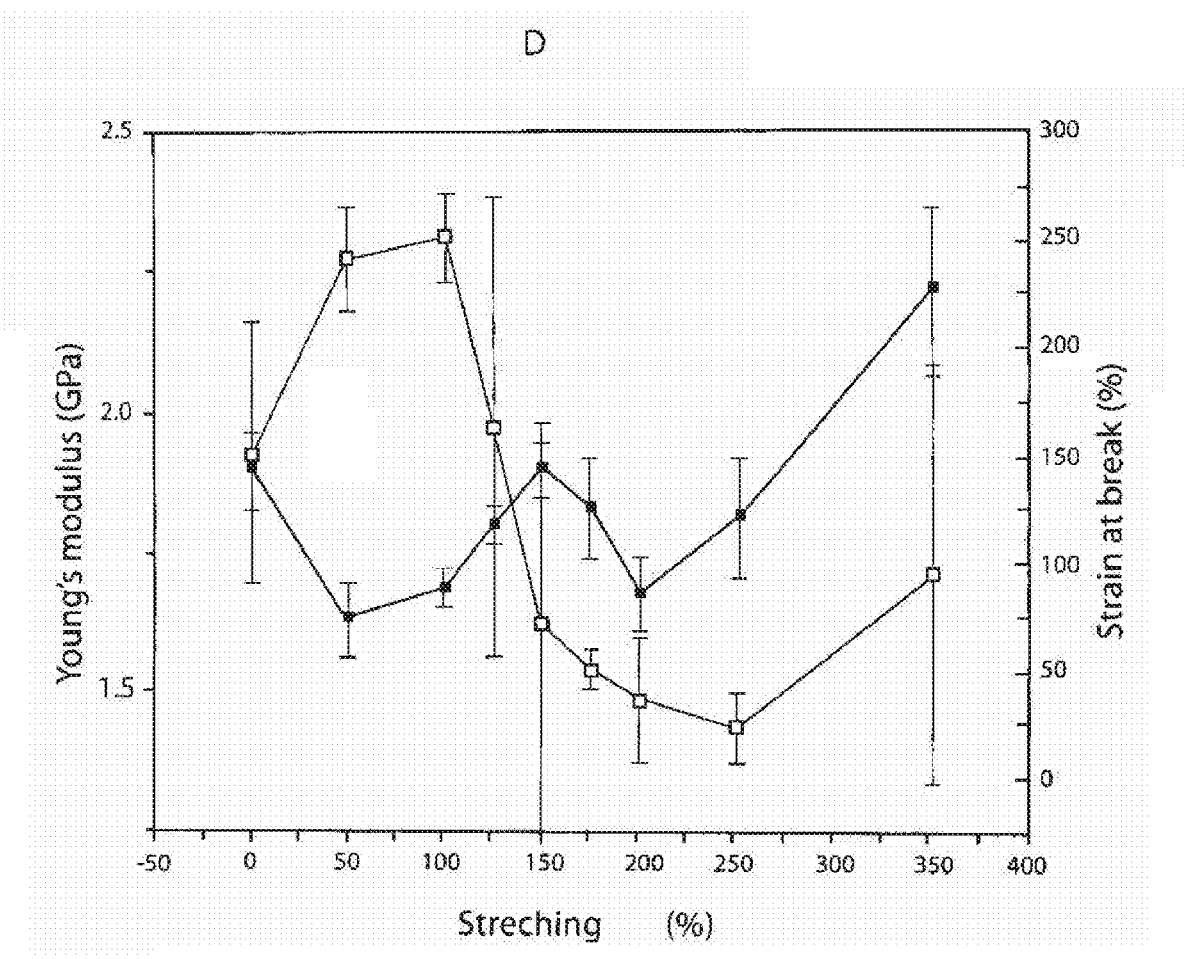
Figure 4E:
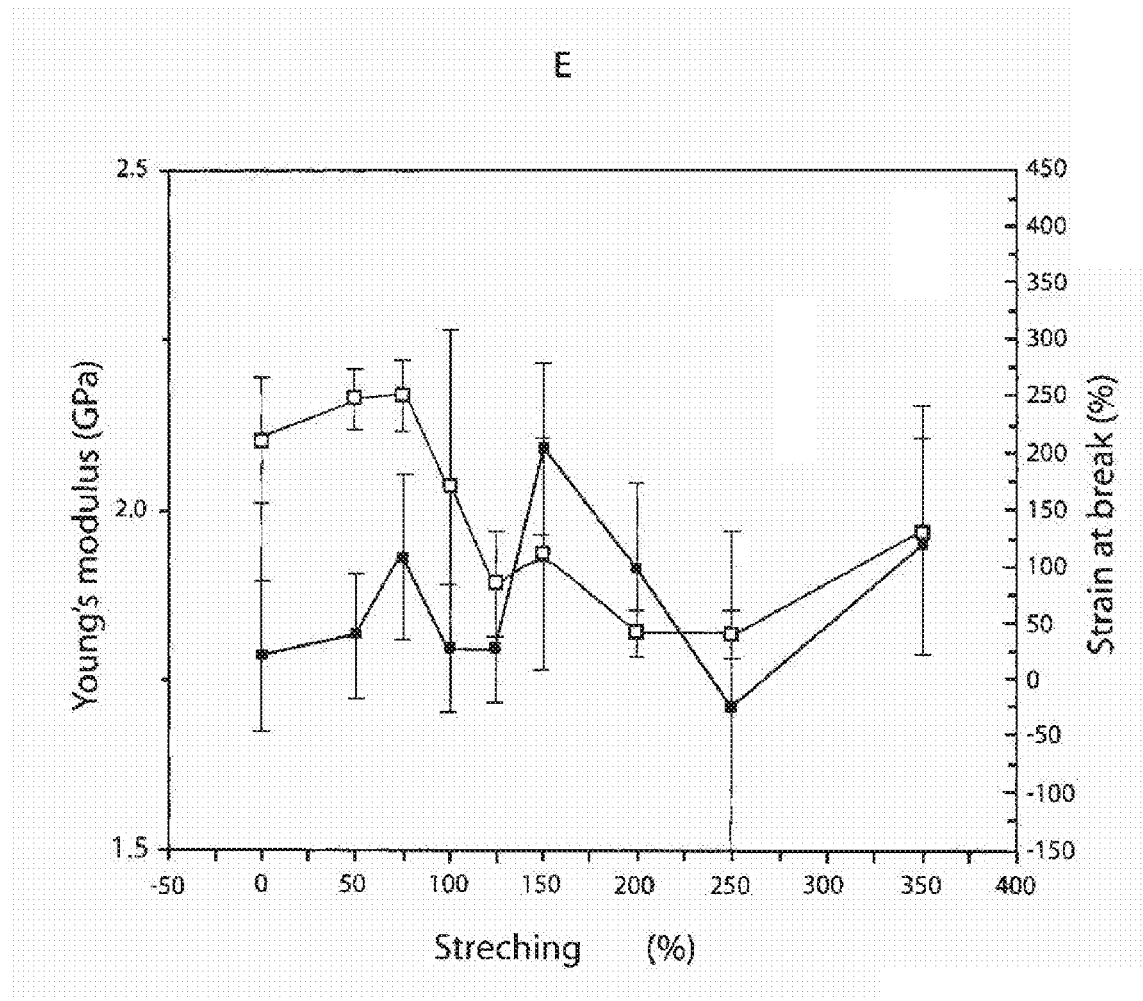
Figure 4F:
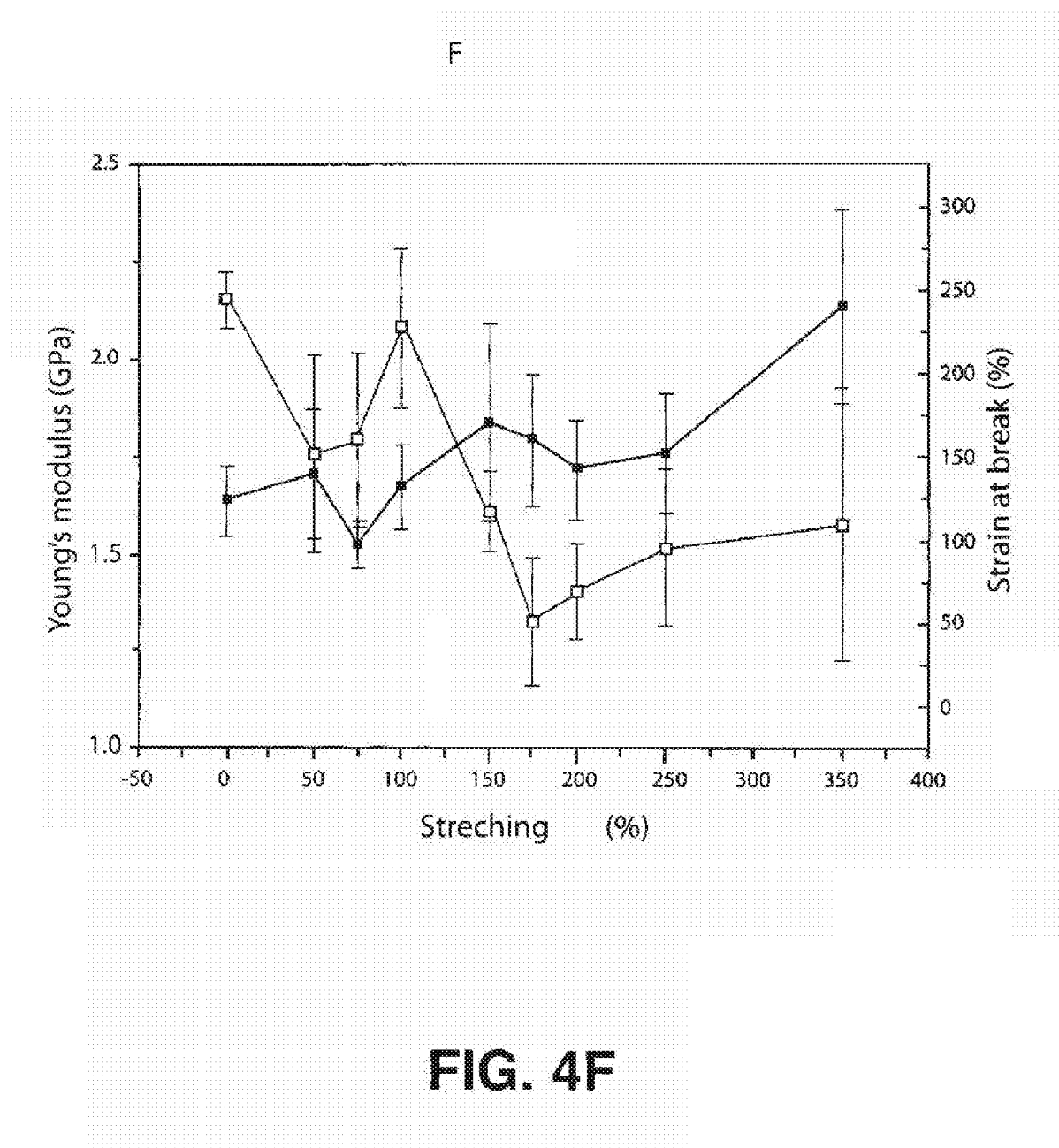
Figure 4G:
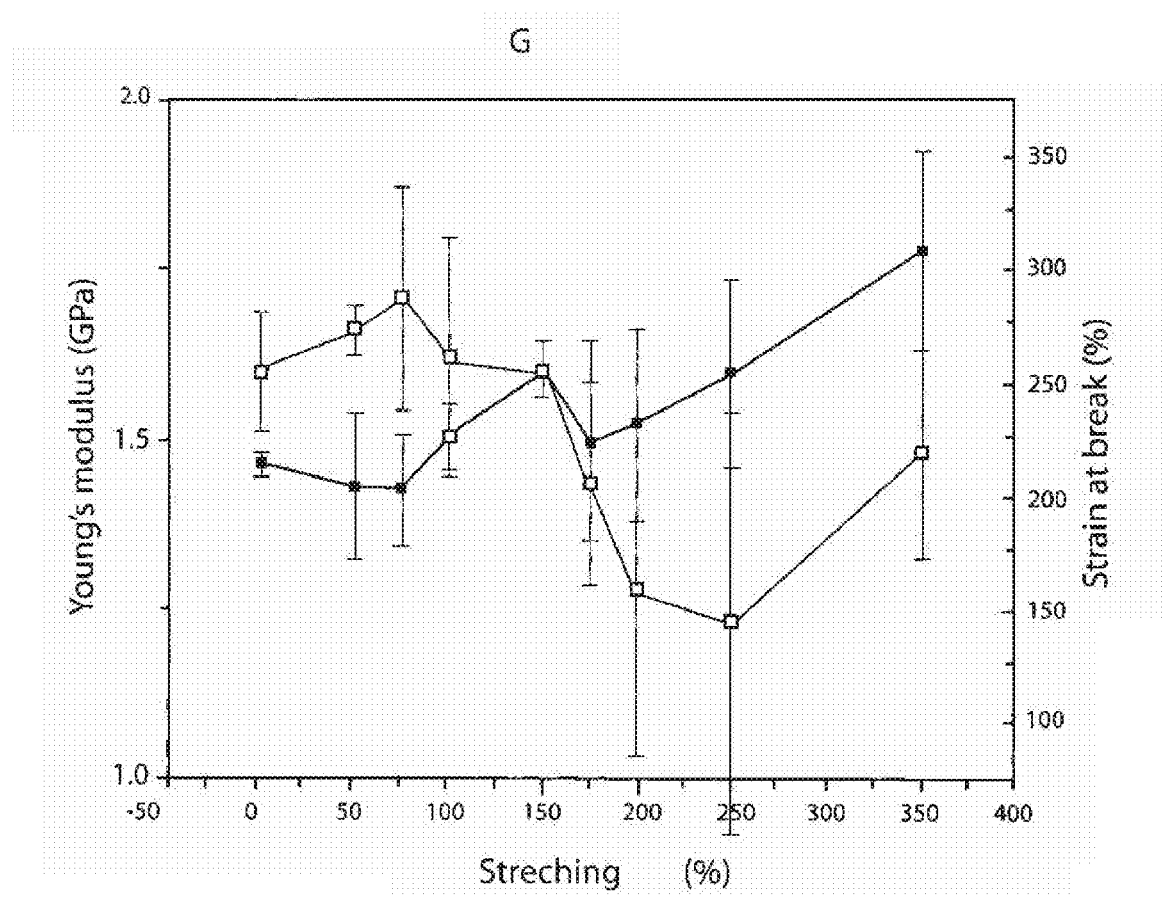
Figure 4H:
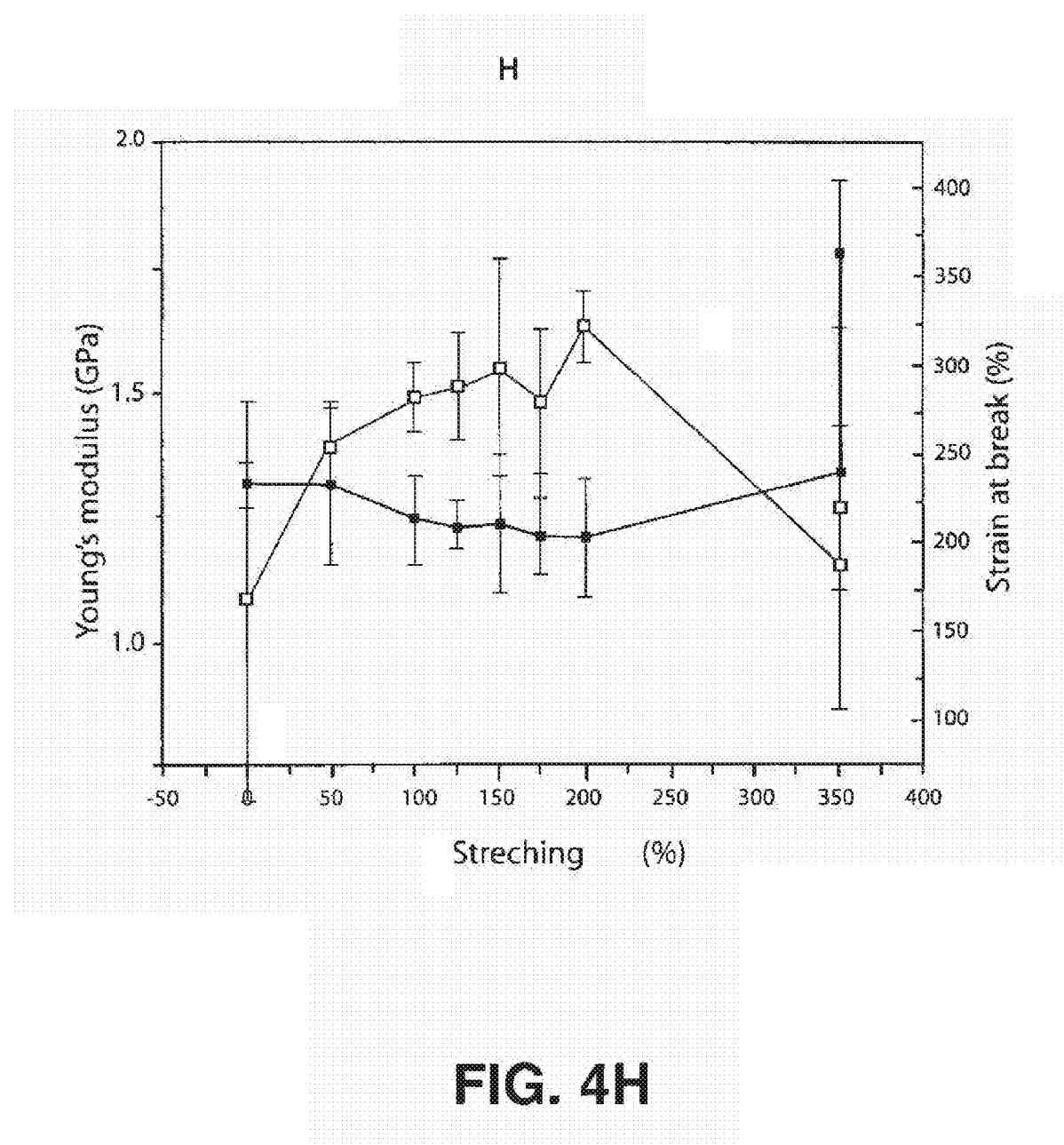

The results were summarized in maps of tensile modulus and strain at break for various stretching (%) values and weight fractions PTMC. FIG. 3 is a graphical representation mapping toughening and reinforcement observed for PLGA:PTMC blends with various weight fractions PTMC (y-axis) at various stretching (%) values (x-axis). The area enclosed within the loop represents blends that have Young's modulus greater than 2 GPa and strain at break greater than 50% parallel to stretching direction. FIG. 3 illustrates that PLGA can be toughened and reinforced at the same time by combining blending and stretching.

Tensile testing was also done in a direction perpendicular to the stretching direction and the results are shown in FIG. 4. FIG. 4 includes graphical representations of Young's modulus (GPa; left y-axis, solid squares) and strain at break (%, right y-axis, open squares) for PLGA and PLGA:PTMC blends at various stretching (%) values perpendicular to stretching direction. FIG. 4A is for PLGA. FIGS. 4B-4H are for PLGA:PTMC blends having PTMC contents of 5 wt %, 10 wt %, 15 wt %, 20 wt %, 25 wt %, 30 wt %, and 40 wt %, respectively. The error bars represent standard deviation calculated from 3 replicate measurements. As indicated in FIG. 4, strain at break of all the blends was significantly increased compared to unstretched pure PLGA (5% strain at break), but modulus decreased. However, both modulus and strain at break of all blends changed very slightly as the PTMC content and stretching (%) were varied, which is different than the properties parallel to the stretching direction, in which modulus substantially increased as stretching (%) increased.

Figure 5:
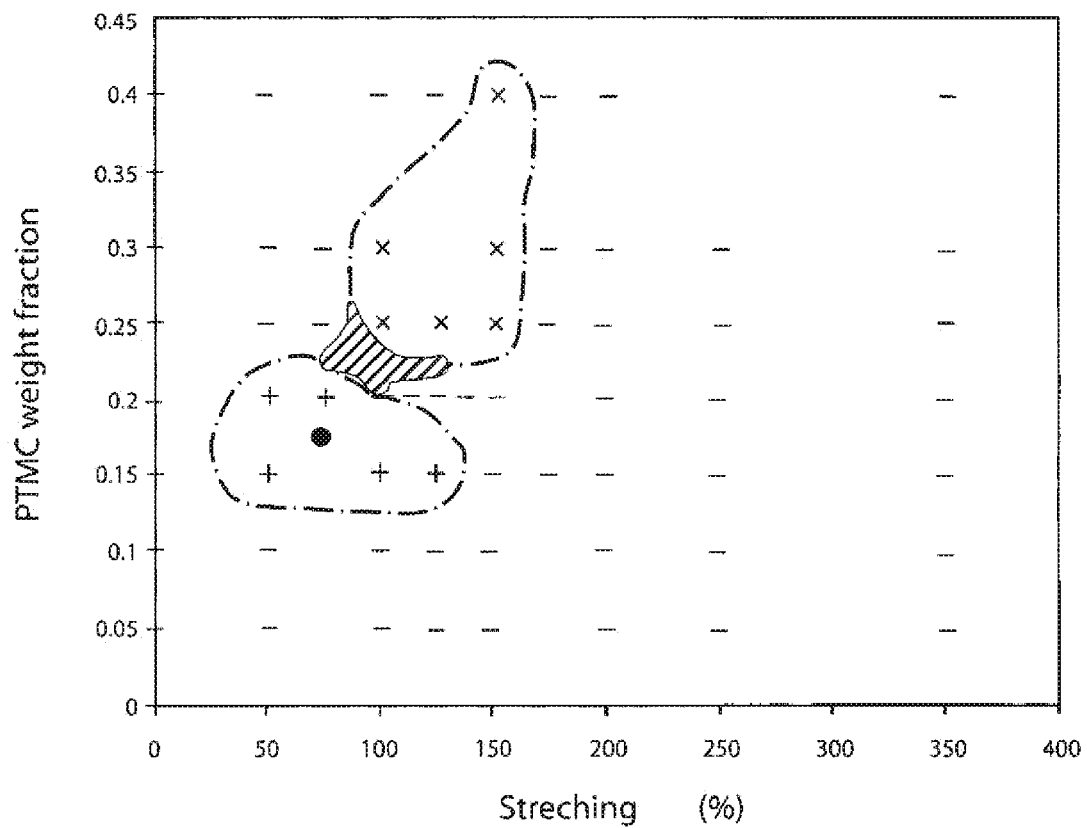
FIG. 5 is a graphical representation mapping toughening and reinforcement observed for PLGA:PTMC blends with various weight fractions PTMC (y-axis) at various stretching (%) values (x-axis). The area enclosed within the upper loop represents blends that have Young's modulus greater than 2 GPa parallel to stretching direction, Young's modulus less than 1.7 GPa perpendicular to stretching direction, and strain at break greater than 50% in both directions. The area enclosed within the lower loop represents blends that have Young's modulus greater than 2 GPa parallel to stretching direction, Young's modulus greater than 1.7 GPa perpendicular to stretching direction, and strain at break greater than 50% in both directions.

Tensile testing results at directions parallel and perpendicular to stretching were combined as is illustrated in FIG. 5. FIG. 5 is a graphical representation mapping toughening and reinforcement observed for PLGA:PTMC blends with various weight fractions PTMC (y-axis) at various stretching (%) values (x-axis). The area enclosed within the upper loop represents blends that have Young's modulus greater than 2 GPa at the direction parallel to stretching, Young's modulus less than 1.7 GPa at a direction perpendicular to stretching, and strain at break greater than 50% in both directions. The area enclosed within the lower loop represents blends that have Young's modulus greater than 2 GPa parallel to stretching direction, Young's modulus greater than 1.7 GPa perpendicular to stretching direction, and strain at break greater than 50% in both directions. The dot in the lower loop represents a blend having a Young's modulus of 2.2 GPa and a strain at break of 128% parallel to stretching direction; and a Young's modulus of 1.8 GPa and a strain at break of 247% perpendicular to stretching direction. The map illustrates that PLGA can be toughened and reinforced at the same time by combined blending and stretching.

Figure 6A:
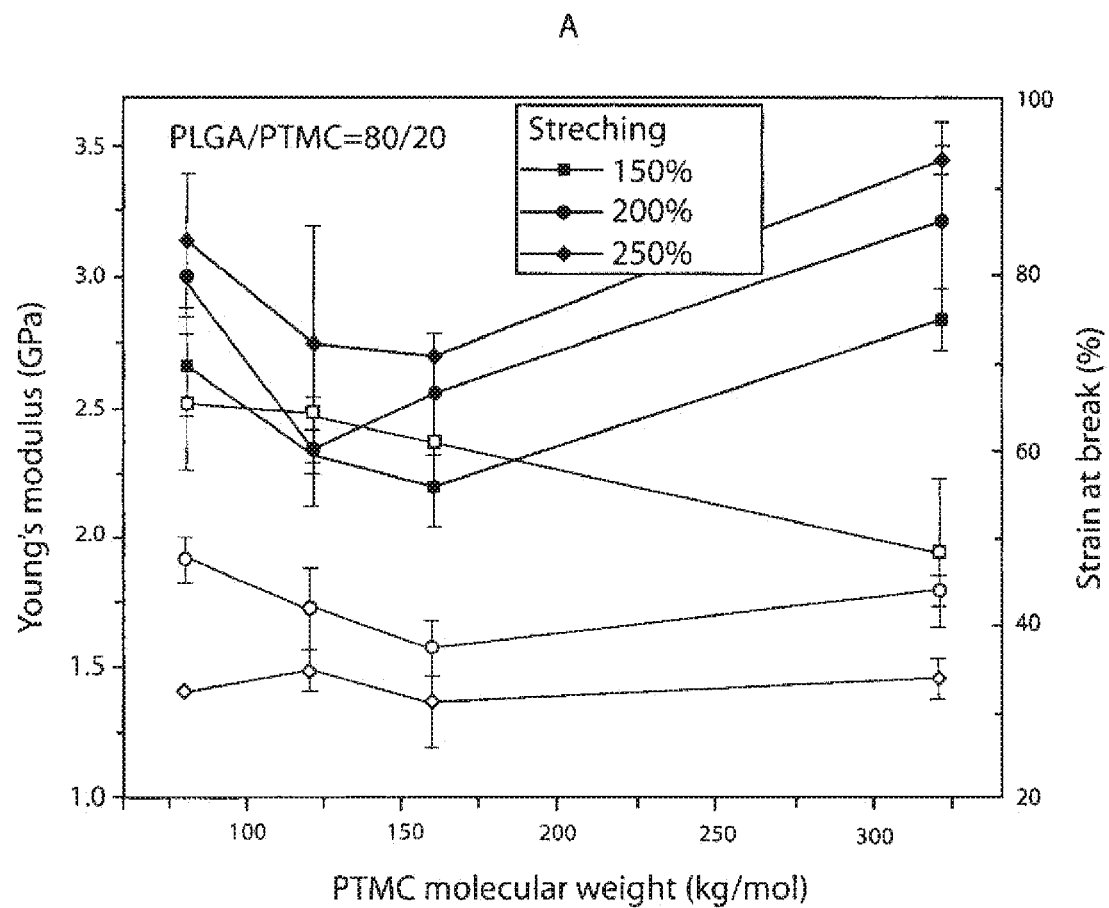
FIGS. 6A and 6B include graphical representations of Young's modulus (GPa; solid symbols, left y-axis) and strain at break (open symbols, right y-axis) for various stretching (%) values parallel to stretching direction for 80:20 (wt:wt) PLGA:PTMC blends.
Figure 6B:
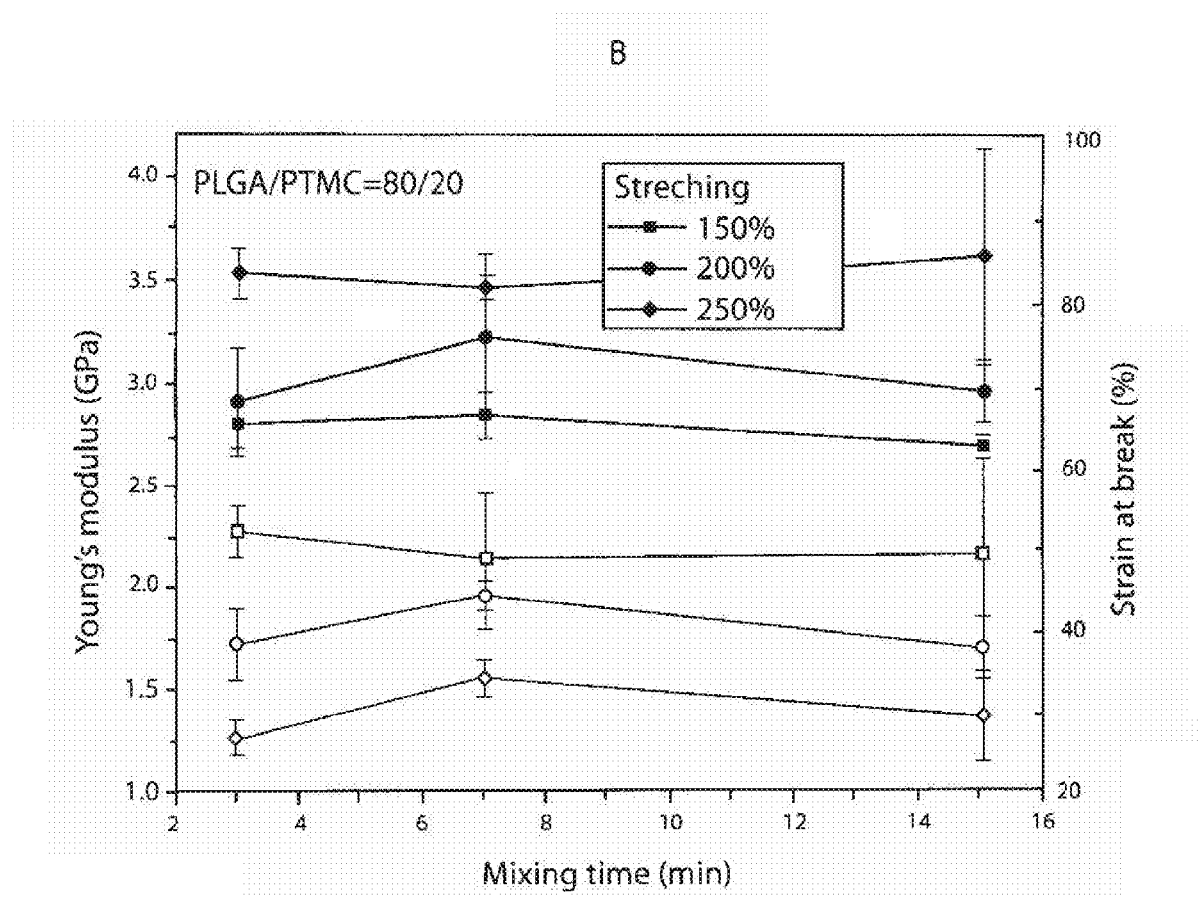
Figure 6C:
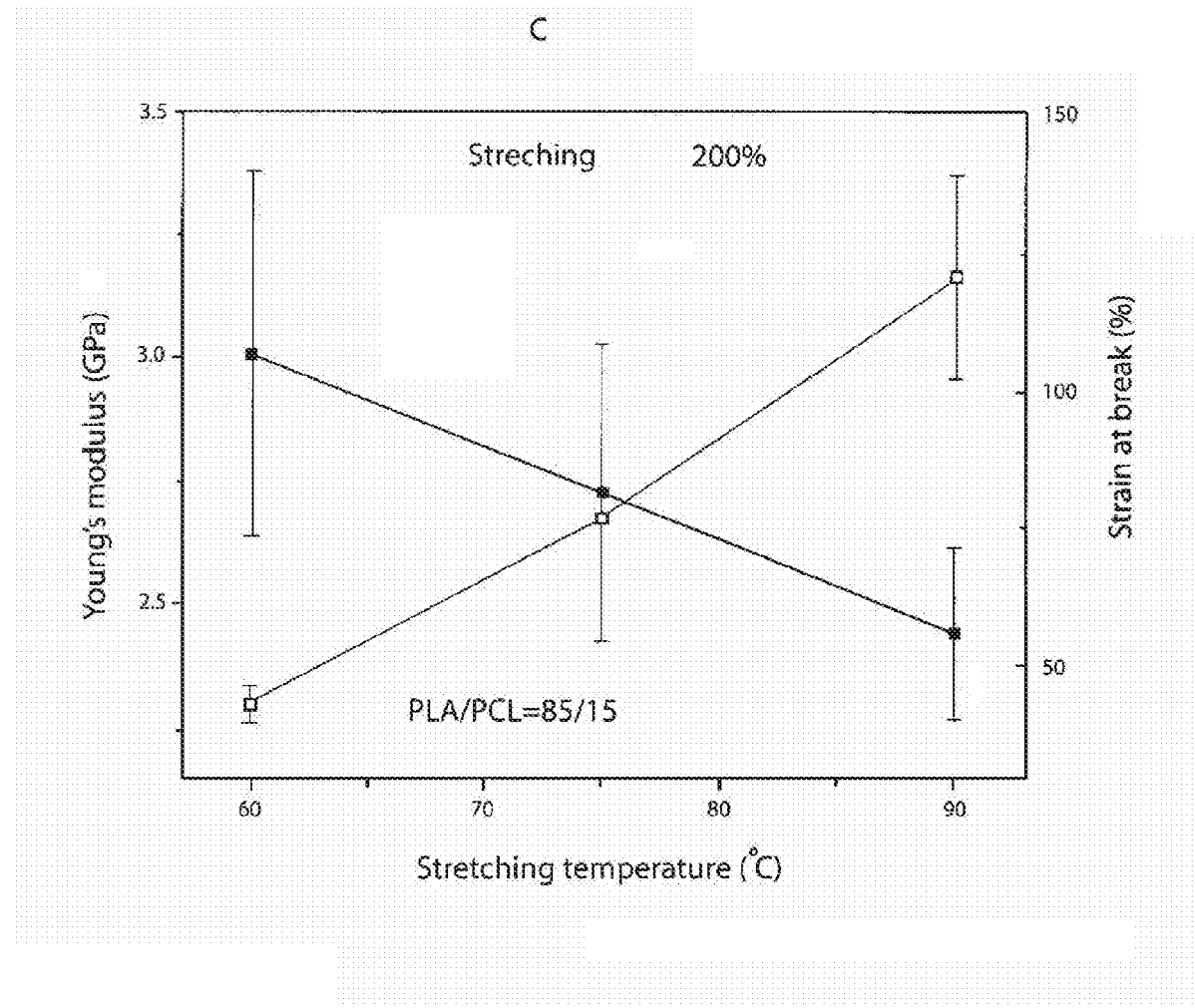
FIGS. 6C and 6D include graphical representations of Young's modulus (GPa; solid squares, left y-axis) and strain at break (%; open squares, right y-axis) at a stretching (%) value of 200% parallel to stretching direction for 85:15 (wt:wt) PLDLLA:PCL blends.
Figure 6D:
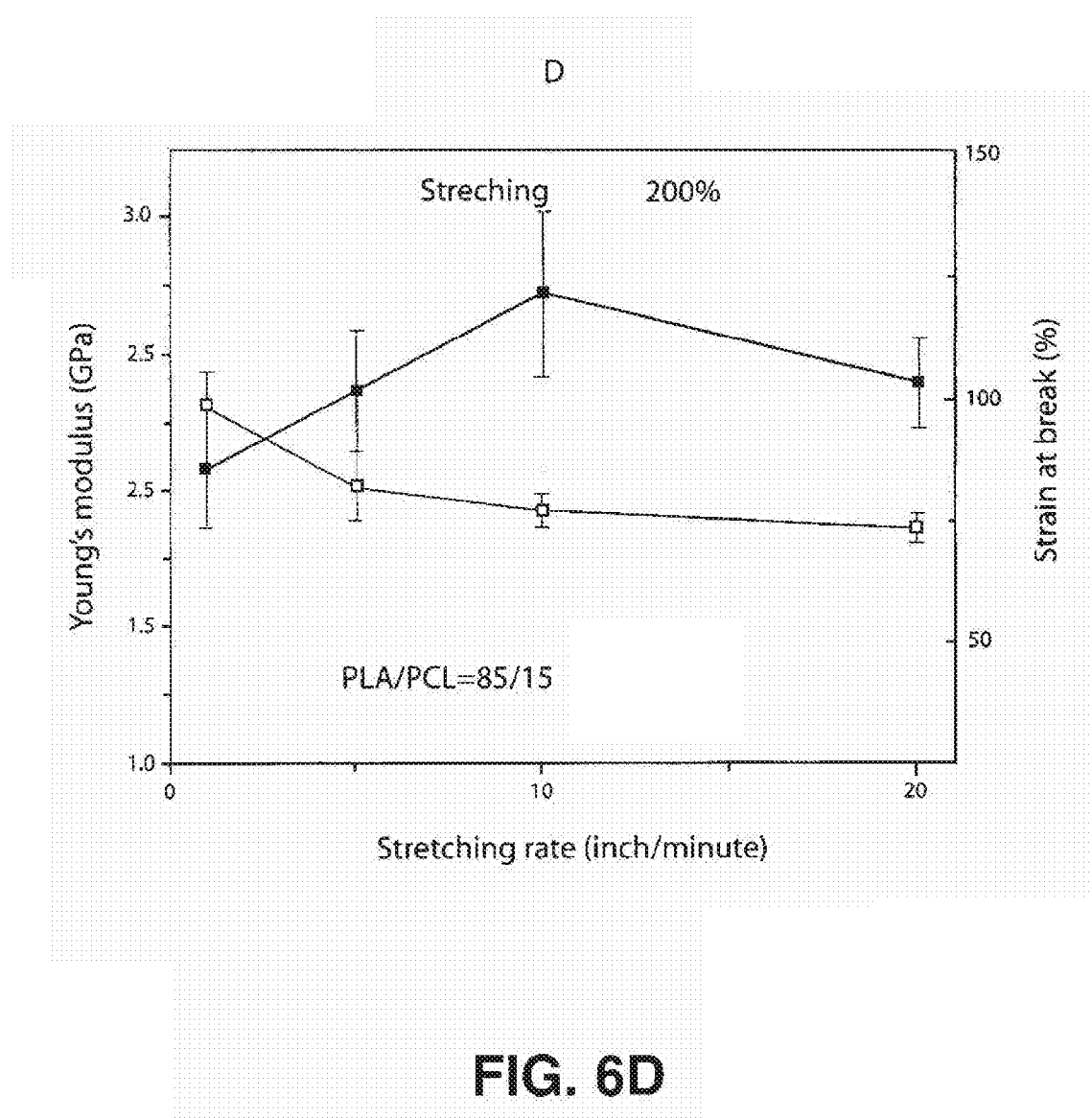

A number of processing parameters were changed to determine how sensitive the properties of the blends were to changing processing conditions. For certain embodiments, an insensitive response or robustness can be preferred for quality and processing control. Results are illustrated in FIG. 6. FIGS. 6A and 6B include graphical representations of Young's modulus (GPa; solid symbols; left y-axis) and strain at break (%; open symbols, right y-axis) for various stretching (%) values parallel to stretching direction for 80:20 (wt:wt) PLGA:PTMC blends. FIG. 6A shows various PTMC molecular weights (kg/mole; x-axis), and FIG. 6B shows various mixing times (minutes; x-axis). FIGS. 6C and 6D include graphical representations of Young's modulus (GPa; left y-axis, solid squares) and strain at break (%; right y-axis, open squares) at a stretching (%) value of 200% parallel to stretching direction for 85:15 (wt:wt) PLDLLA:PCL blends. FIG. 6C shows various stretching temperatures (° C.; x-axis), and FIG. 6D shows various stretching rates (inches/minute; x-axis). The error bars represent standard deviation calculated from 3 replicate measurements. Except for cooling rate, the properties of blends were not very sensitive to the processing parameters studied. Rapid cooling appears to favor higher modulus (rigidity). A PLDLLA:PCL blend stretched for 200% had a 3.1 GPa modulus if cooled with water (rapid cooling). If cooled with air (slower cooling), the modulus was 1.8 GPa.

FIG. 7 illustrates transmission electron micrographs showing microstructures of unstretched PLGA:PTMC blends for various PTMC contents. Samples were stained with $RuO_4$ to show PTMC domains as dark areas. FIGS. 7A-7D are for 10 wt %, 20 wt %, 30 wt %, and 40 wt % PTMC, respectively. At low PTMC contents (e.g., 10 wt %), the PTMC domain was present as a discrete phase. At higher PTMC contents (e.g., 40 wt %), the PTMC phase and the PLGA phase approached co-continuity.

Figure 8:
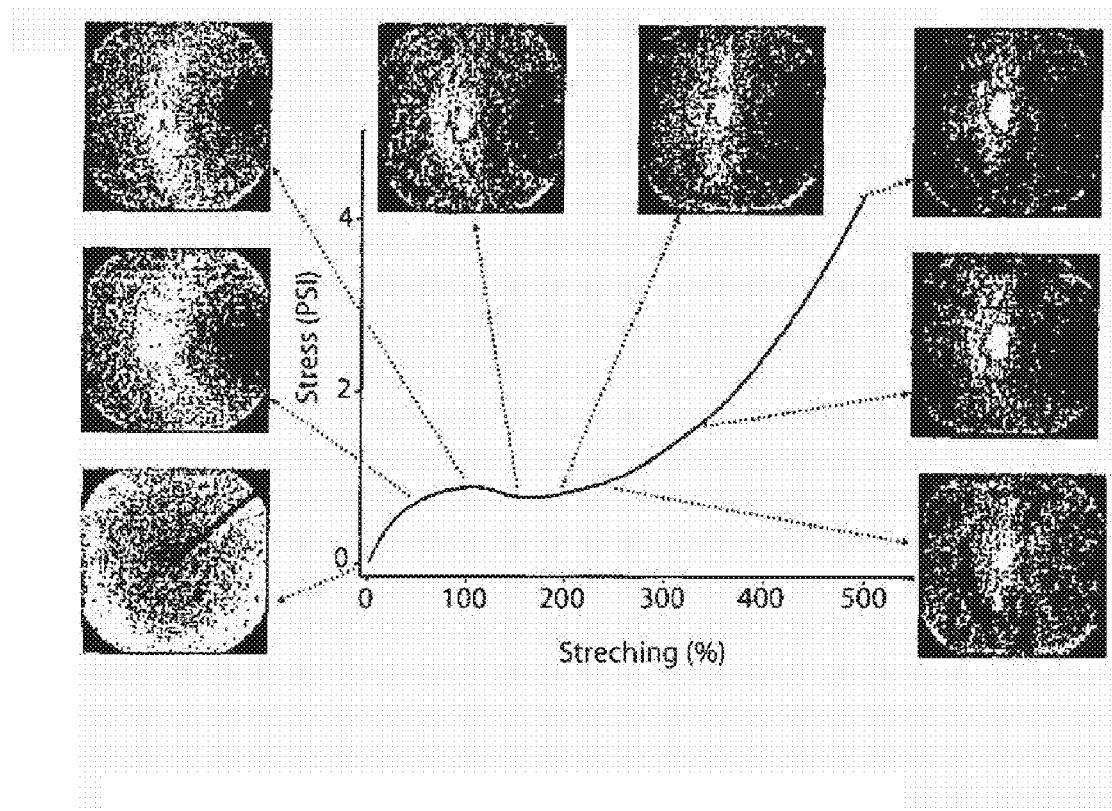
FIG. 8 illustrates a plot of wide angle X-ray scattering for an 80:20 (wt:wt) PLGA:PTMC blend for various stretching (%) values. The X-ray beam is perpendicular to the stretching direction. The white spots for stretching (%) values greater than 100% indicated chain orientation.

After the blends were stretched, there were two changes. The first change was chain orientation as evidenced from the wide angle X-ray scattering. FIG. 8 illustrates a plot of wide angle X-ray scattering for an 80:20 (wt:wt) PLGA:PTMC blend for various stretching (%) values. The X-ray beam is perpendicular to the stretching direction. An amorphous blend (before stretching) has a dispersive scattering ring. As the stretching (%) increased, a few scattering spots appeared. The white spots for stretching (%) greater than 100% indicated chain orientation. The intensity of the scattering spots was increased with stretching (%), indicating stretching induced chain orientation within the blends. Chain orientation is one dimensional ordered structure. X-ray radiation is scattered at preferred directions leading to the appearance of white spots.

Figure 7A:
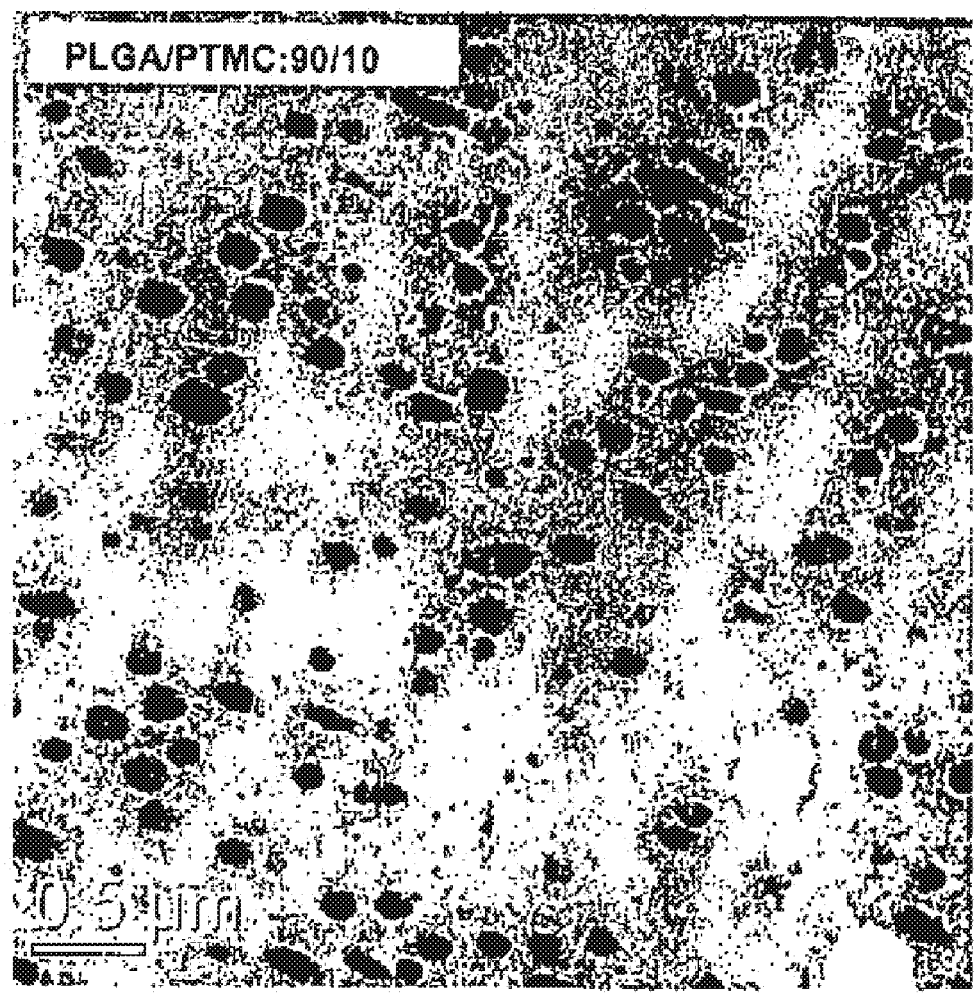
FIGS. 7A-7D are for 10 wt %, 20 wt %, 30 wt %, and 40 wt % PTMC, respectively.
Figure 7B:
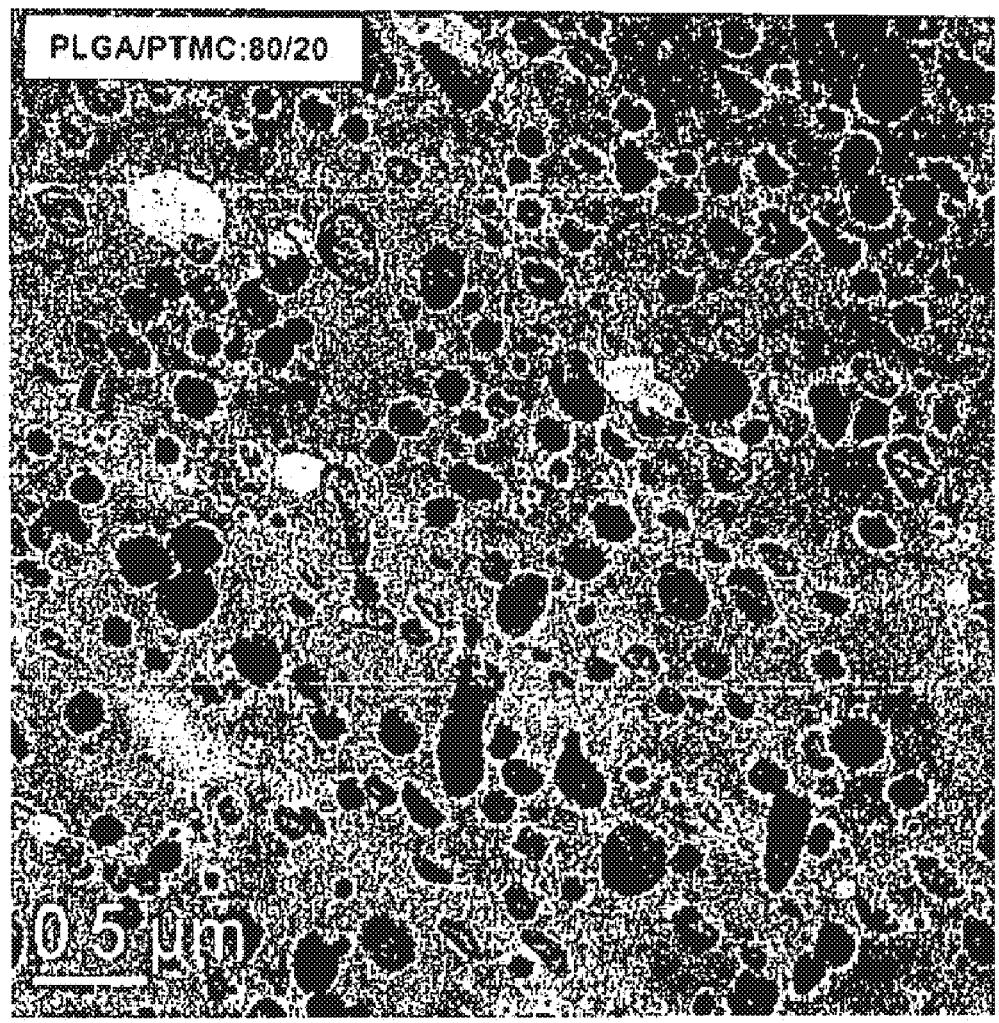
Figure 7C:
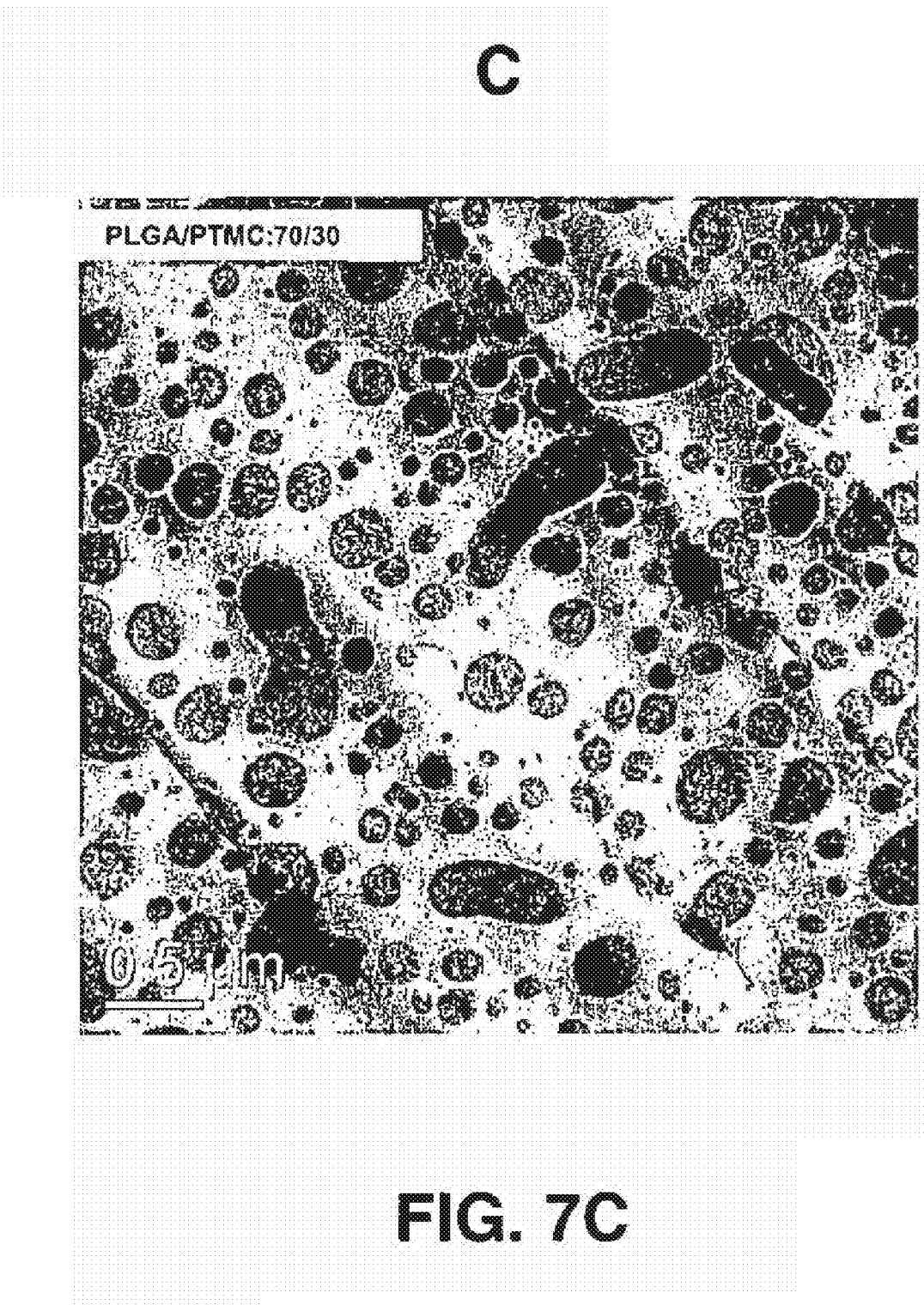
Figure 7D:
Figure 9:
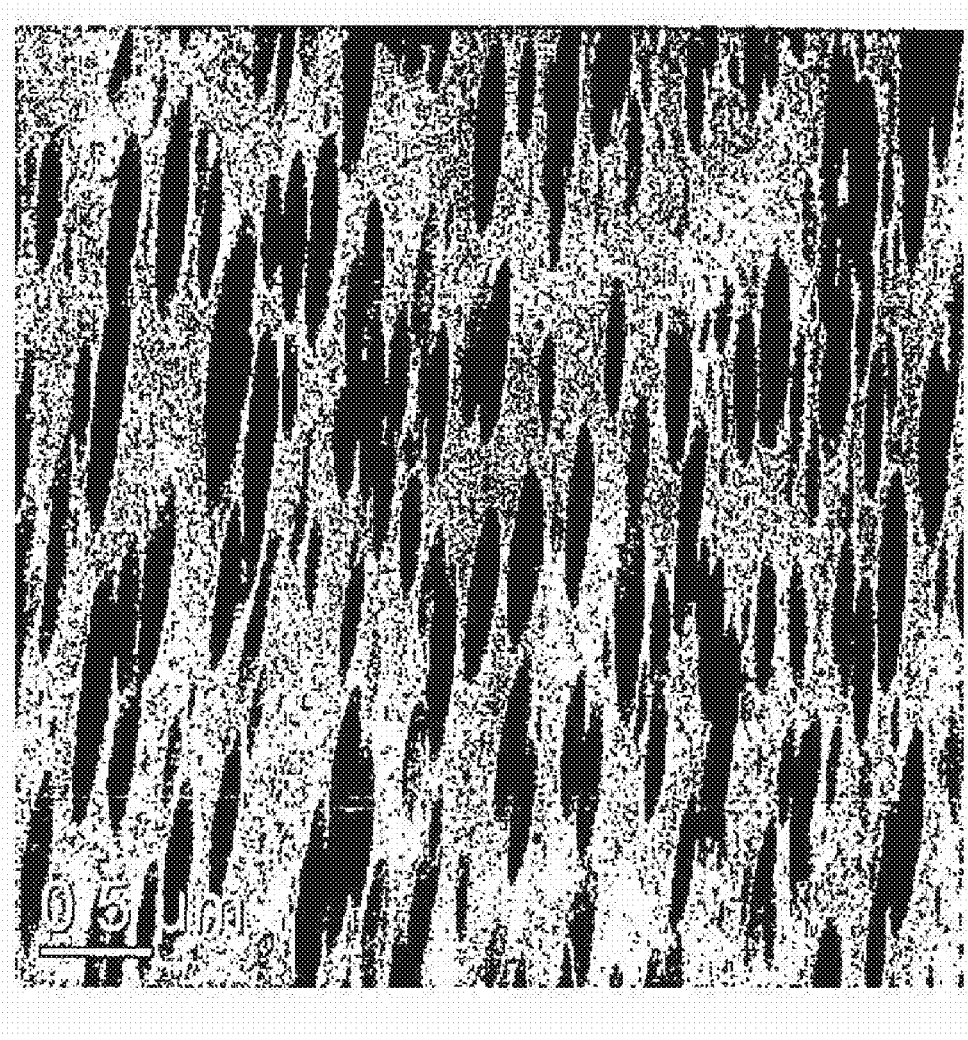
FIG. 9 illustrates a transmission electron micrograph showing morphology for an 80:20 (wt:wt) PLGA:PTMC blend after being stretched vertically with a stretching (%) value of 500%. Before stretching, the PTMC domains in a PLGA:PTMC (80:20) blend were discrete round particles dispersed in a PLGA continuous phase as illustrated in FIG. 7B.

Micrometer scale structural changes also occur. FIG. 9 illustrates transmission electron micrographs showing morphology for an 80:20 (wt:wt) PLGA:PTMC blend after being stretched vertically with a stretching (%) value of 500%. Before stretching, the PTMC domains in a PLGA:PTMC (80:20) blend were discrete round particles dispersed in a PLGA continuous phase as illustrated in FIG. 7B. As shown in FIG. 9, the PTMC domains in a PLGA:PTMC (80:20) blend were stretched to shapes elongated in the stretching direction. This domain stretching increased the aspect ratio of the PTMC phase. Dispersed phases with higher aspect ratios can lead to toughening effects.

Figure 10:
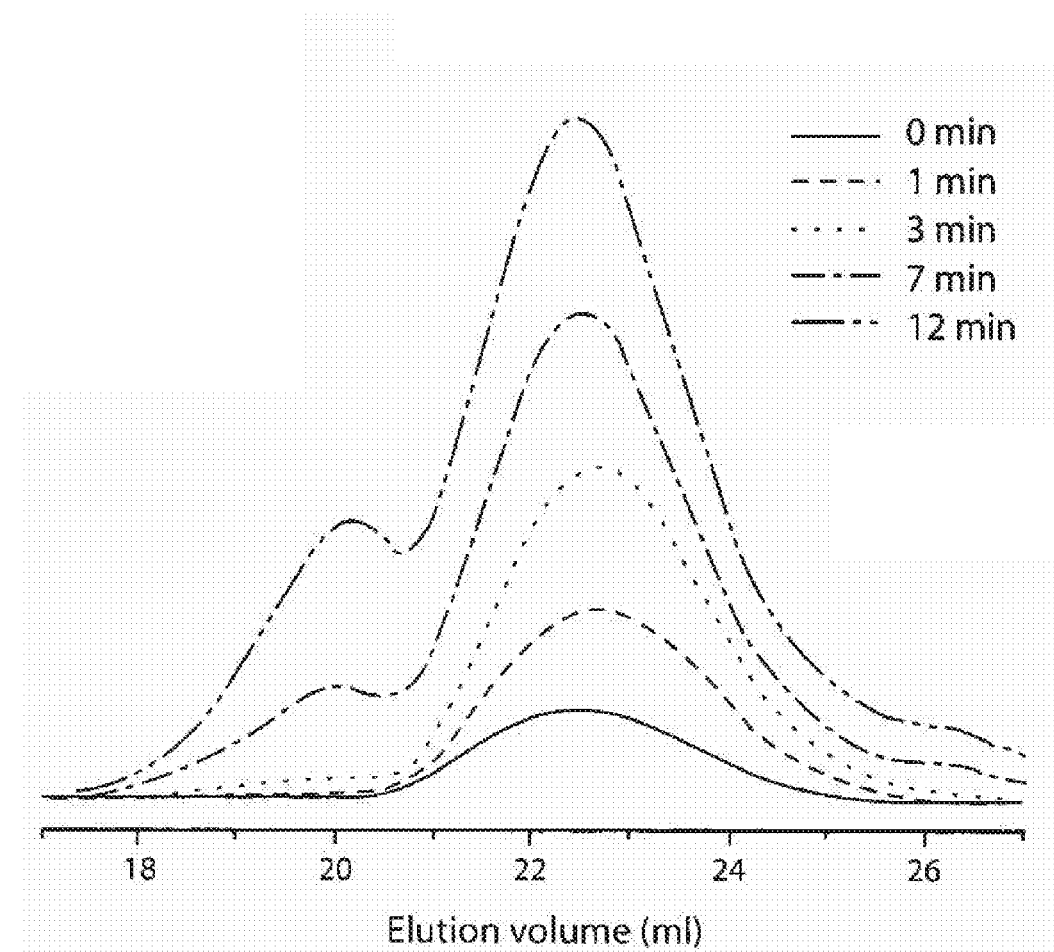
FIG. 10 shows gel permeation chromatography (GPC) elution volume plots at various mixing times for fluorescent labeled PTMC:PLGA blends. The eluting curve for pure fluorescent labeled PTMC was labeled as 0 minutes mixing time. For mixed samples, a second peak at lower elution volume (higher molecular weight) was observed and increased as mixing time increased.

REACTIVE BLENDING EXPERIMENTS: In a first experiment, a fluorescent active compound (9-anthracenemethanol) was used to initiate a low molecular weight (approximately 12 kg/mole) PTMC sample to give a labeled PTMC that can be detected by a fluorescent detector used with high pressure liquid chromatography (HPLC). The labeled PTMC was blended with a PLGA sample (LG857, B1, approximately 600 kg/mole) in a ratio of PLGA:PTMC of 80:20 (wt:wt). The blend was analyzed with gel permeation chromatography (GPC). FIG. 10 shows gel permeation chromatography (GPC) elution volume curves of fluorescent labeled PTMC:PLGA blends mixed for various times. The eluting curve for pure fluorescent labeled PTMC was labeled as 0 minutes mixing time. For mixed samples, a second peak (at lower elution volume, higher molecular weight) was observed and increased as mixing time increased. The results suggest that new materials (e.g., PTMC:PLGA copolymers) were formed.

Figure 11A:
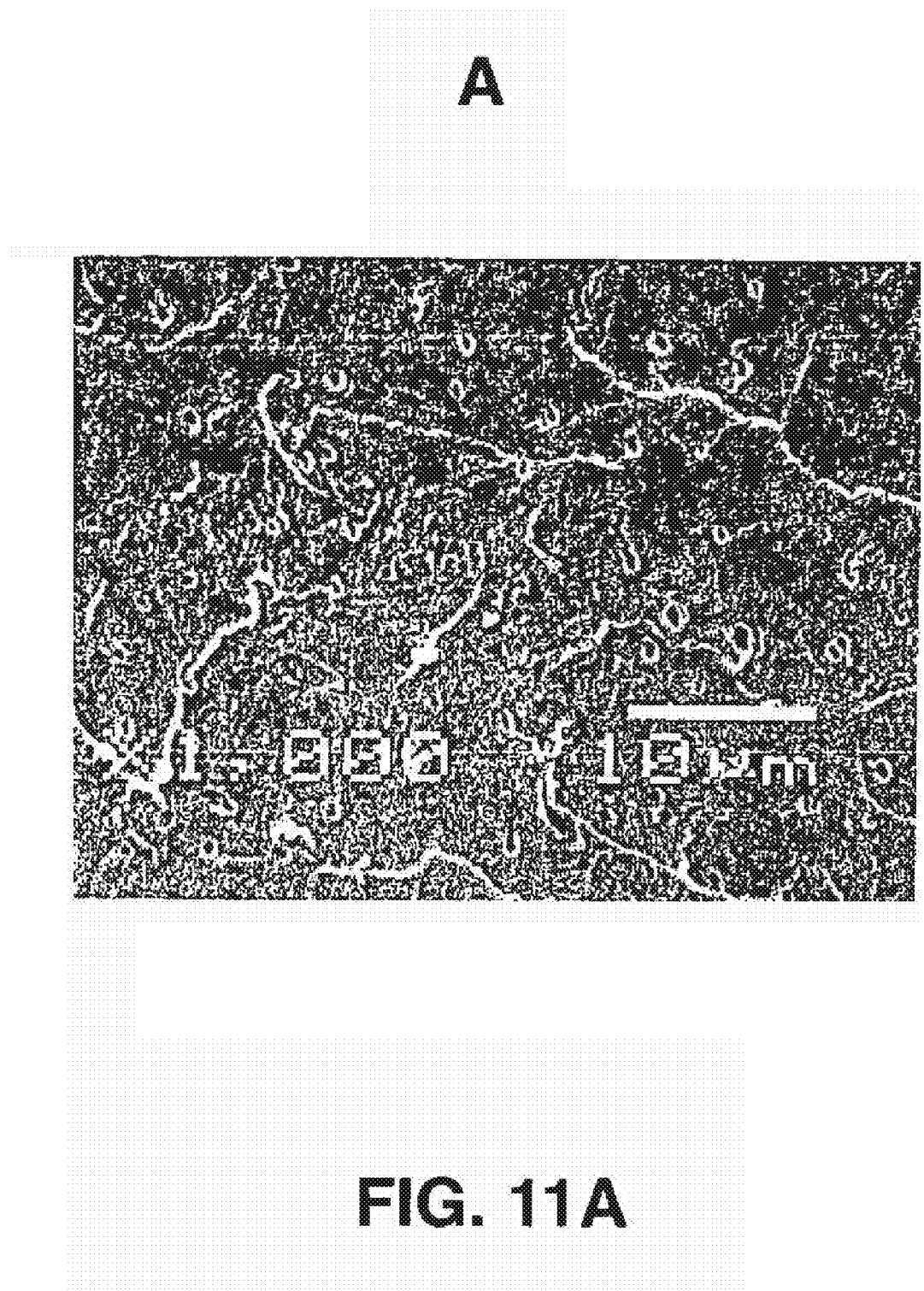
FIGS. 11A and 11B illustrate scanning electron micrographs for cross-sections of 80:20 (wt:wt) PLGA:PTMC blends that were (A) solvent blended and (B) melt blended at 215° C. Voids were evident in the solvent blended sample but not in melt blended sample.
Figure 11B:
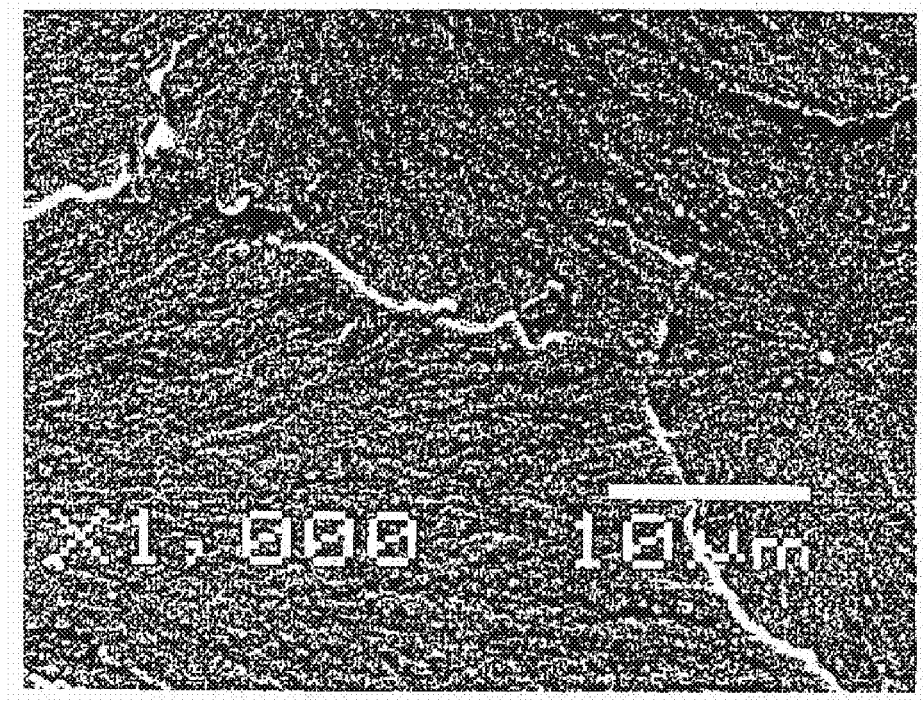
Figure 11C:
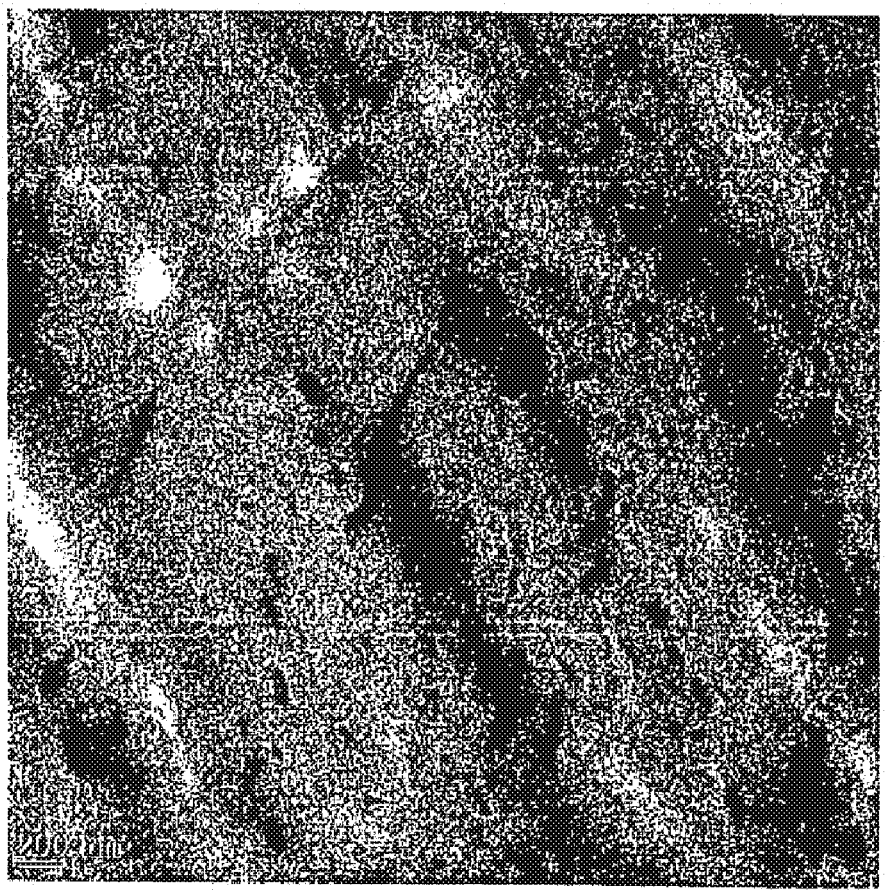
FIGS. 11C and 11D illustrate transmission electron micrographs of an 82.5:17.5 (wt:wt) PLGA:PTMC blend that was (C) cross-sectioned parallel to stretching, and (D) cross-sectioned perpendicular to stretching.
Figure 11D:
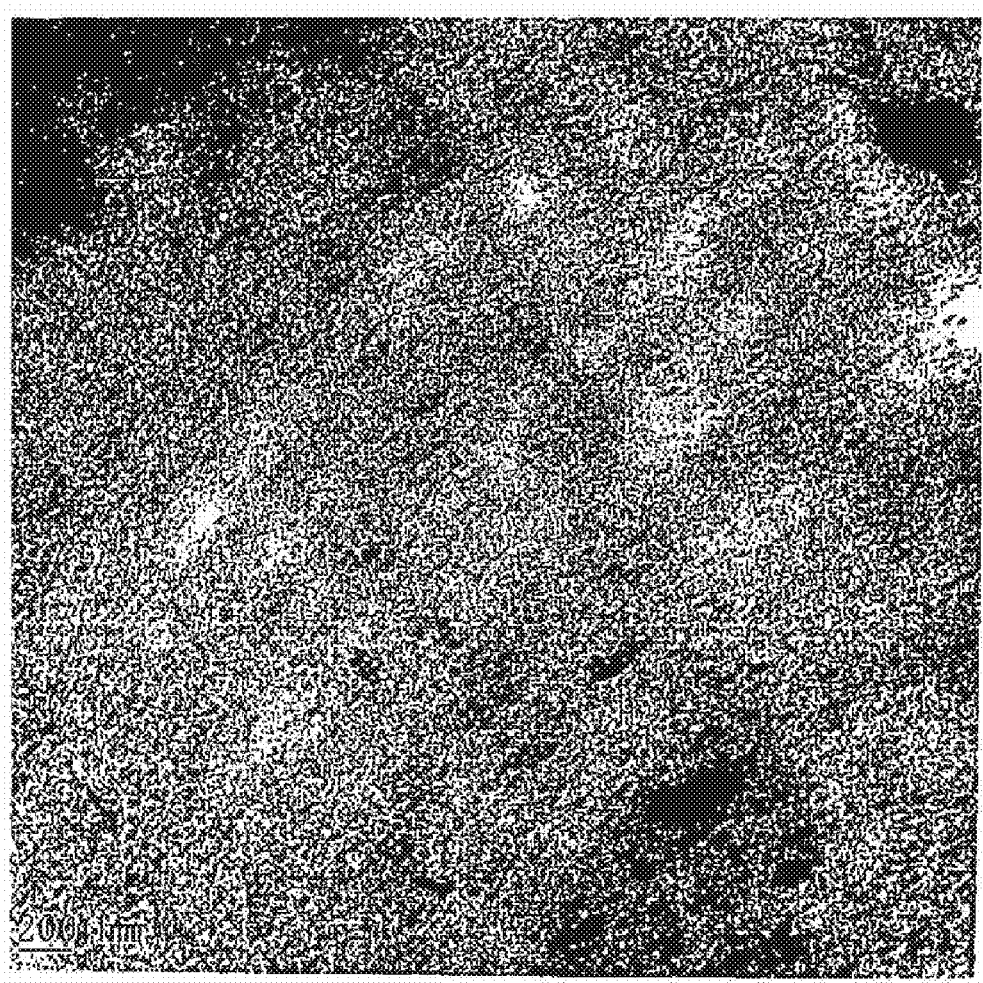

A second experiment was run comparing the bonding strength between the PTMC and PLGA phases in blends that were melt-mixed and blends that were solvent blended at ambient temperature. FIG. 11 illustrates scanning electron micrographs for cross-sections of an 80:20 (wt:wt) PLGA: PTMC blend that were (A) solvent blended, and (B) melt blended at 215° C. Voids were evident in the solvent blended sample but not in melt blended sample, which is consistent with higher bond strength between the PTMC and PLGA phases in blends that were melt-mixed. FIGS. 11C and 11D illustrate transmission electron micrographs of an 82.5:17.5 (wt:wt) PLGA:PTMC blend that was (C) cross-sectioned parallel to stretching, and (D) cross-sectioned perpendicular to stretching. Higher bond strength between phases in the melt blended sample could be attributed, for example, to the formation of new materials (e.g., PTMC:PLGA copolymers) through trans-esterification reactions, for example. Notably, trans-esterification reactions would not be expected to readily occur in samples that were solvent blended at low temperatures.

DEGRADATION TESTING: The samples for degradation tests included pure PLGA (unstretched), pure PTMC (unstretched), unstretched PLGA:PTMC (82.5:17.5) blends, and uniaxially stretched PLGA:PTMC (82.5:17.5) blends (stretching (%)=100%). Disc samples were placed in PBS solution (pH7.4) and incubated at 37° C. for various times. The degradation media was refreshed as needed to keep the pH unchanged. All the discs were initially weighed; weighed after testing for various times with surface water being removed by absorbing with a paper towel; and weighed after drying in a vacuum oven at 55° C. for 24 hours. Unstretched blend samples were also incubated at 55° C., 70° C., and 85° C. for accelerated aging studies.

Figure 12A:
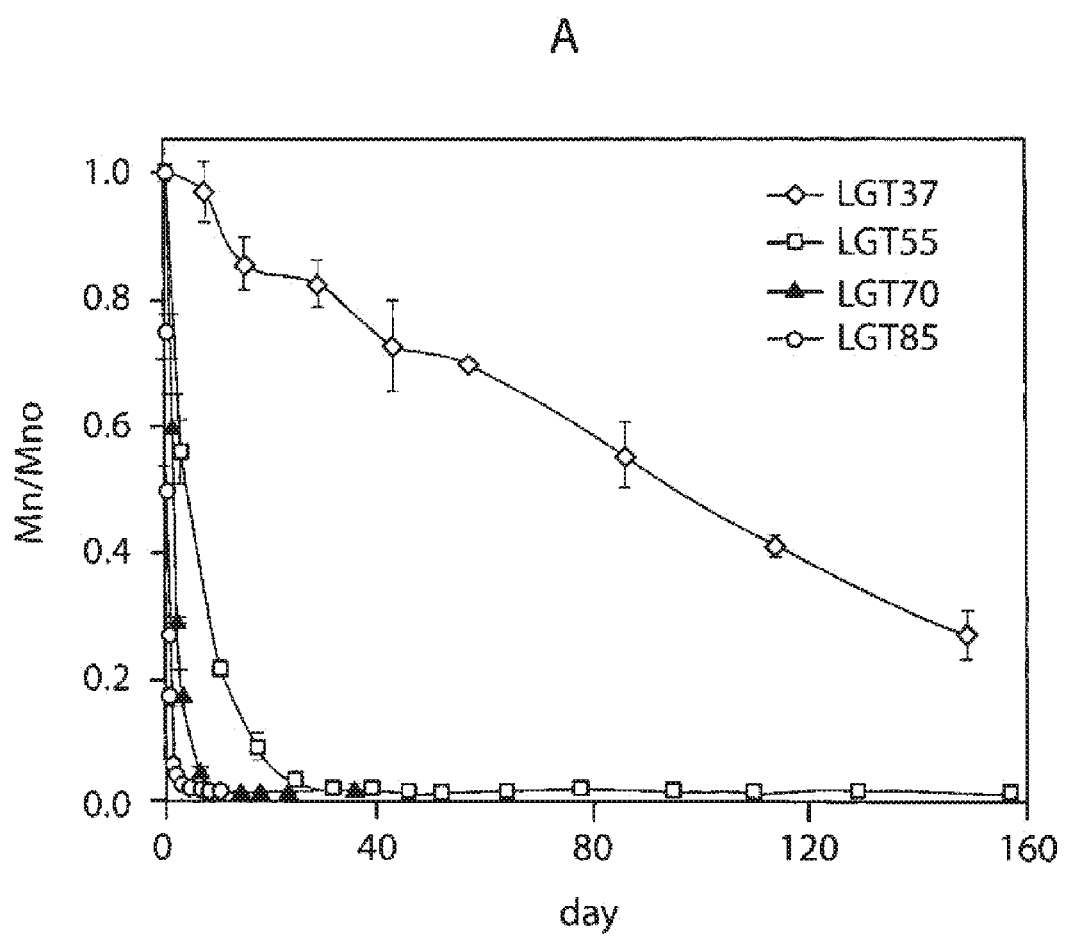
FIG. 12A is a graphical representation of molecular weight normalized to the initial molecular weight (y-axis) for an 82.5:17.5 (wt:wt) PLGA:PTMC blend as function of degradation time (days; x-axis) at various testing temperatures.
Figure 12B:
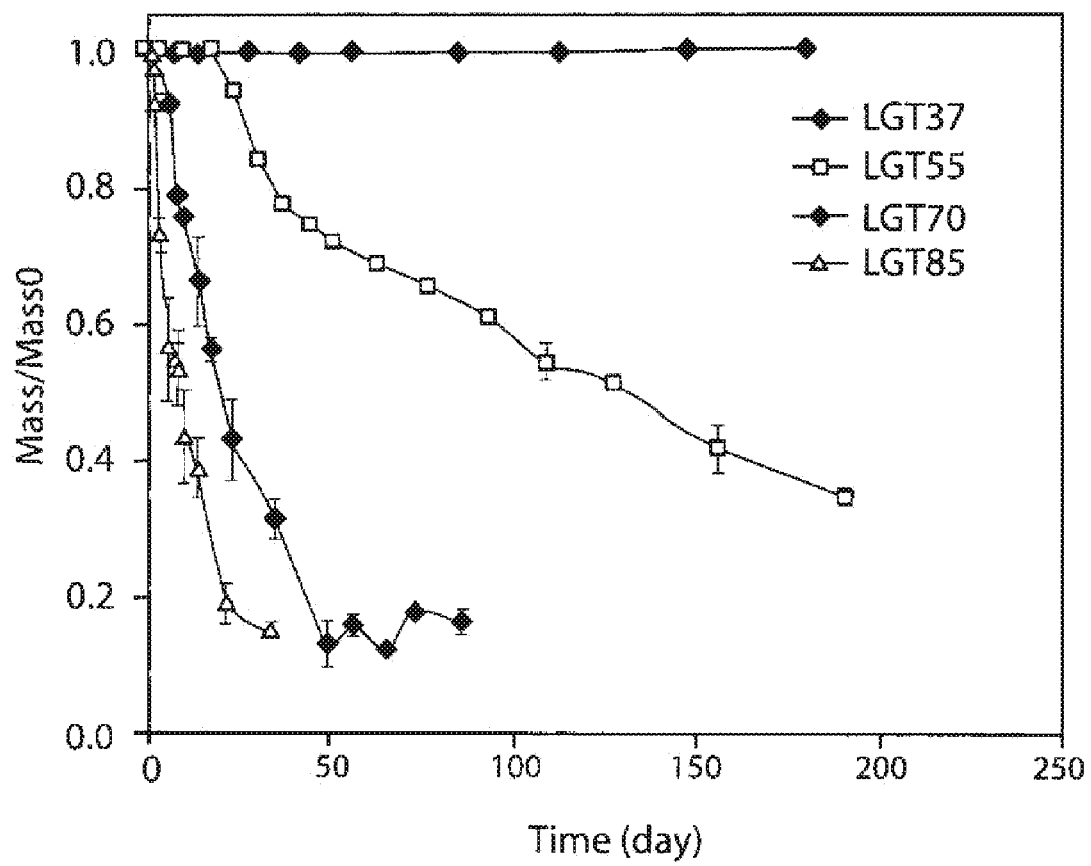
FIG. 12B is a graphical representation of mass normalized to the initial values (y-axis) for an 82.5:17.5 (wt:wt) PLGA:PTMC blend as function of degradation time (days; x-axis) at various testing temperatures. Testing temperatures were 37° C. (LGT37), 55° C. (LGT55), 70° C. (LGT70), and 85° C. (LGT85).

Degradation of unstretched blends at various temperatures was shown in FIG. 12. FIG. 12A is a graphical representation of molecular weight normalized to the initial molecular weight (y-axis) for an 82.5:17.5 (wt:wt) PLGA:PTMC blend as a function of degradation time (days; x-axis) at various testing temperatures. FIG. 12B is a graphical representation of mass normalized to the initial values (y-axis) for an 82.5:17.5 (wt:wt) PLGA:PTMC blend as function of degradation time (days; x-axis) at various testing temperatures. Testing temperatures were 37° C. (LGT37), 55° C. (LGT55), 70° C. (LGT70), and 85° C. (LGT85). Degradation at higher temperatures was faster as indicated by the faster changes in measure $M_n$ and mass.

Figure 13A:
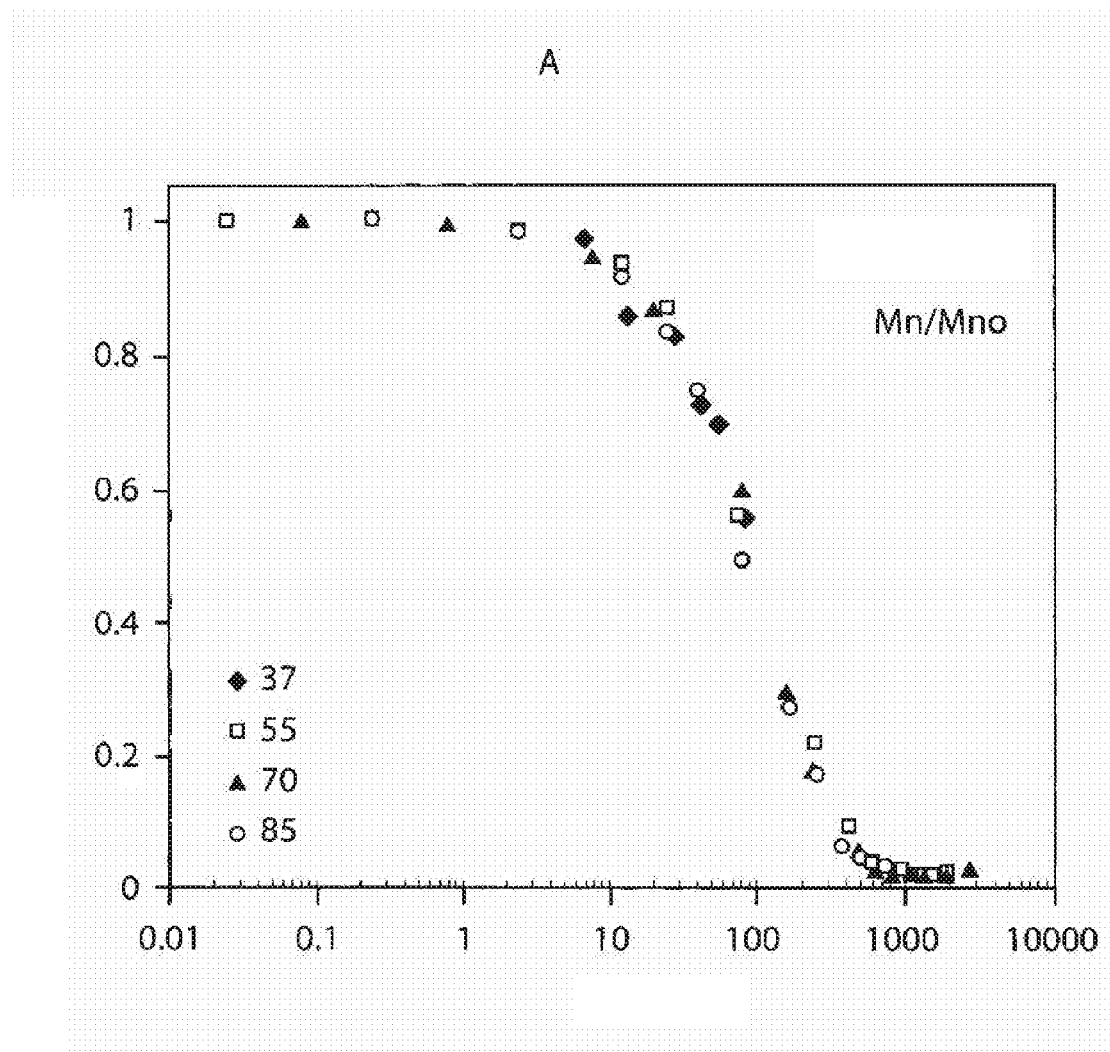
FIG. 13A is a graphical illustration of a master degradation curve constructed by shifting degradation data (e.g., FIG. 12A) obtained at various temperatures.
Figure 13B:
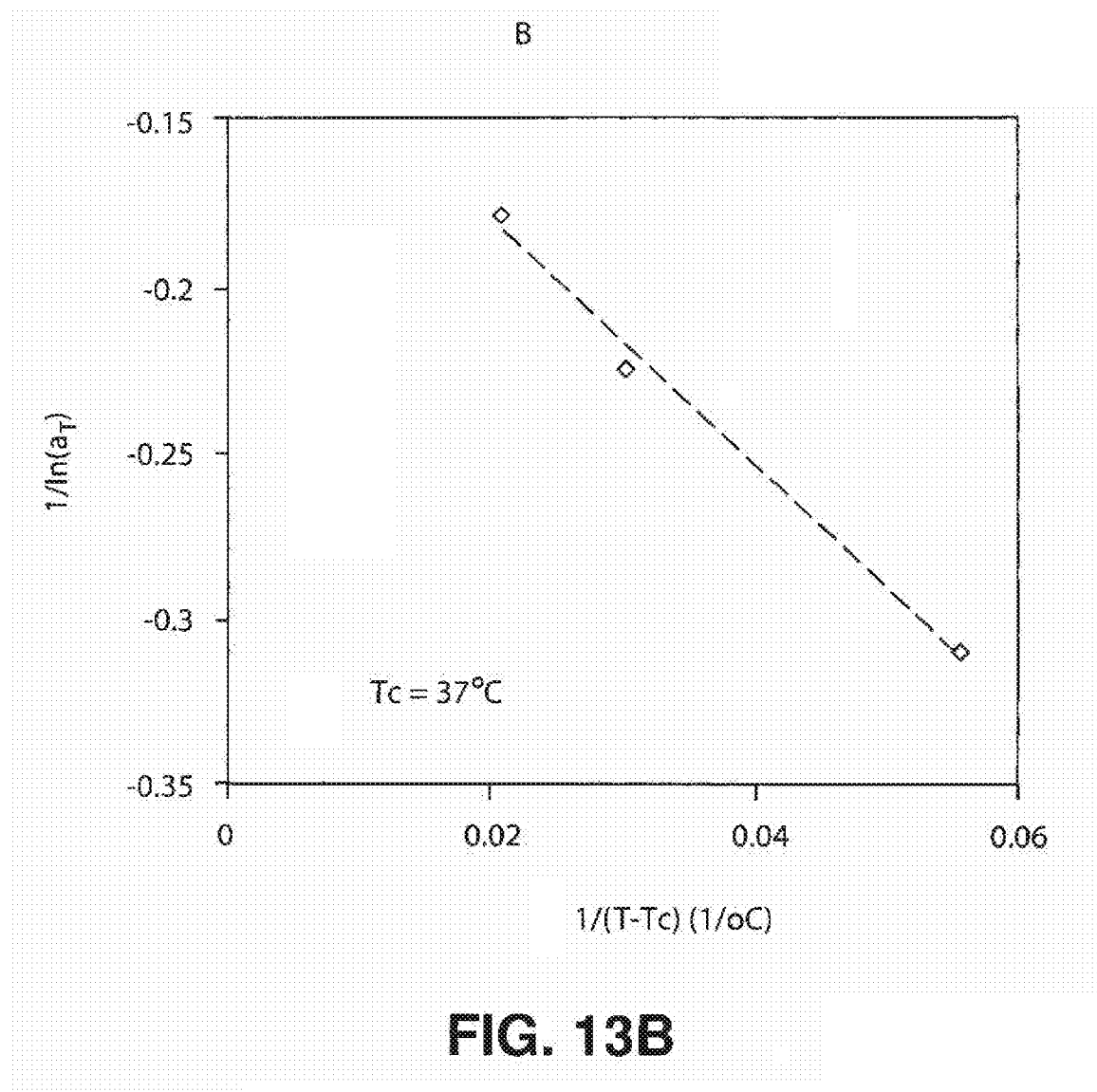
FIG. 13B is a graphical illustration of the reciprocal of the logarithm of the shifting factors as a function of 1/(T−Tc). The linear relationship indicates that the degradation of the PLGA:PTMC blend follows the time-temperature superposition principle.

FIG. 13A is a graphical illustration of a master degradation curve constructed by shifting degradation data (e.g., FIG. 12A) obtained at various temperatures. In order to confirm that this data shifting is physically meaningful, the reciprocal of the logarithm of the shifting factors (aT) was plotted as a function of 1/(T−Tc) in FIG. 13B. The reference temperature Tc was 37° C. The linear relationship indicates that the degradation of the PLGA:PTMC blend follows the time-temperature superposition principle, which says that that kinetic processes of polymers at higher temperature for shorter time is equivalent to behavior at lower temperature for longer time, according to the following equation:

$$\ln(a_T) = \frac{-C_1(T-Tc)}{C_2 + (T-Tc)} \quad (1)$$

wherein $C_1$ and $C_2$ are materials specific parameters and Tc is reference temperature (37° C. for the present case). Equation 1 can be rearranged into the following linear form:

$$\frac{1}{\ln(a_T)} = -\frac{1}{C_1} - \frac{-C_2}{C_1(T-Tc)} \quad (2)$$

Data fitting gave $C_1$=9.5 and $C_2$=35.1. The master curve in FIG. 13A predicts it would take an order of magnitude of 1000 days for the degradation to complete.

Figure 14A:
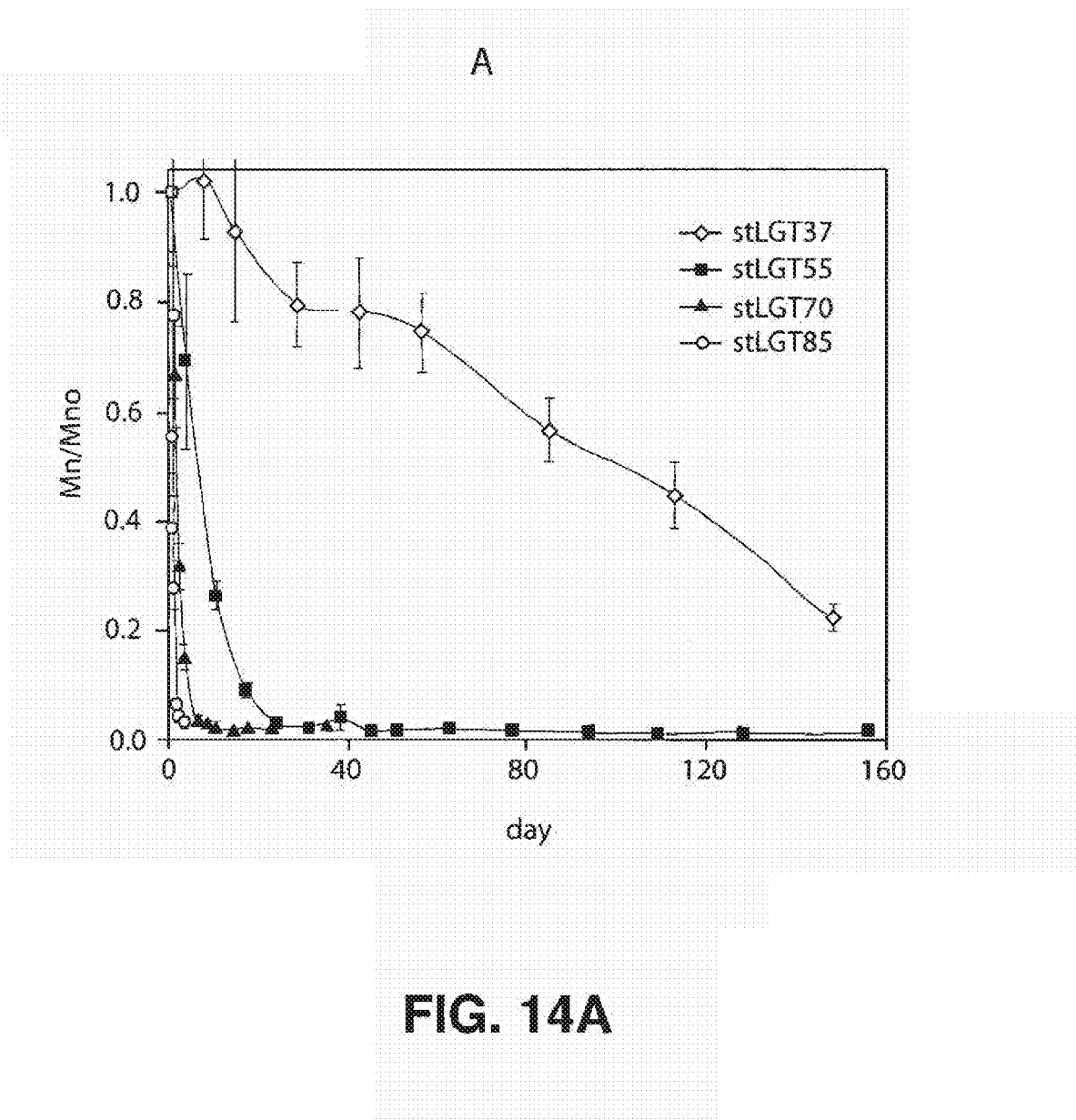
FIG. 14A is a graphical representation of molecular weight normalized to the initial molecular weight (y-axis) for an 82.5:17.5 (wt:wt) PLGA:PTMC 100% stretched blend as function of degradation time (days; x-axis) at various testing temperatures.
Figure 14B:
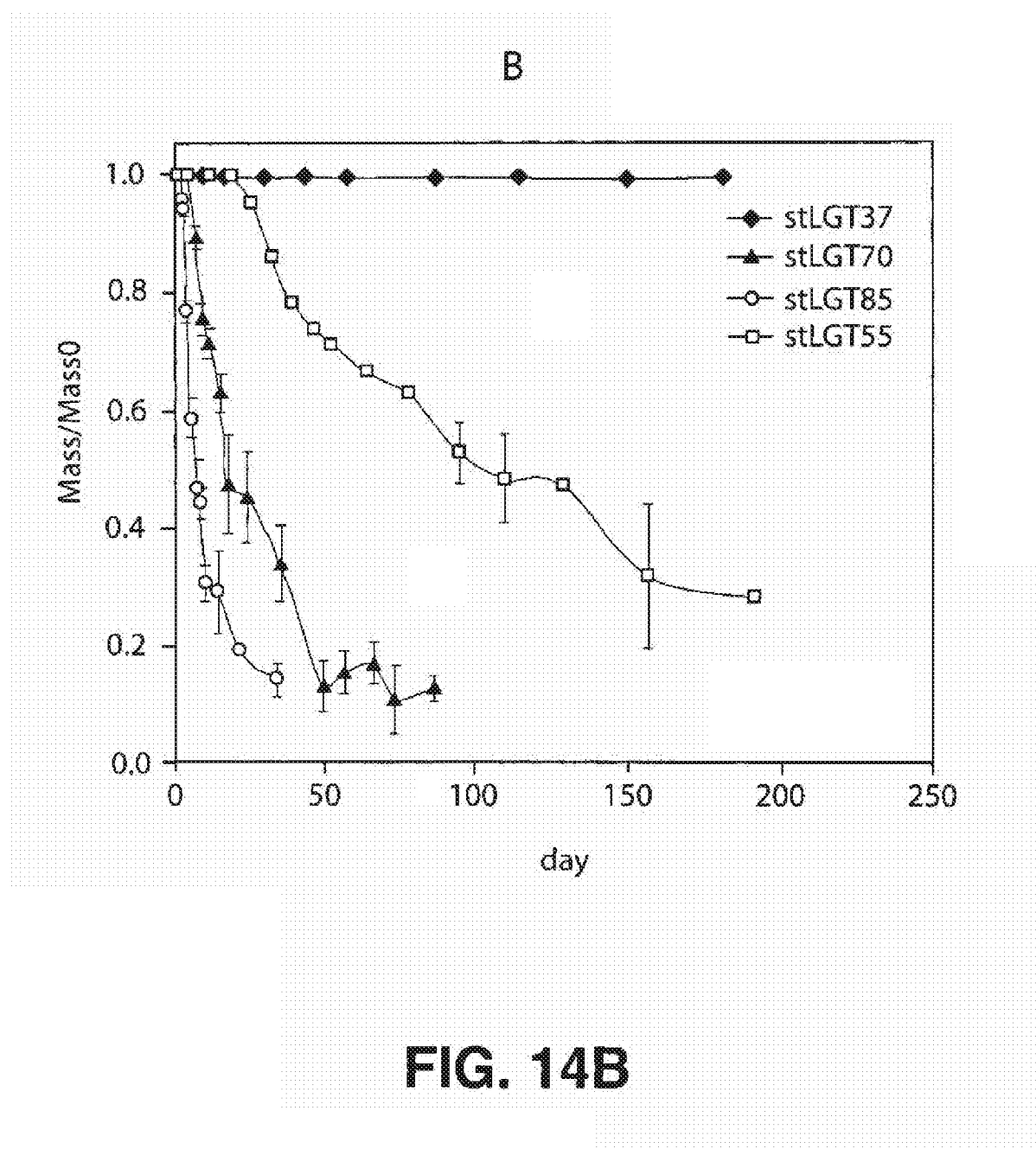
FIG. 14B is a graphical representation of mass normalized to the initial values (y-axis) for an 82.5:17.5 (wt:wt) PLGA:PTMC 100% stretched blend as function of degradation time (days; x-axis) at various testing temperatures. Testing temperatures were 37° C. (stLGT37), 55° C. (stLGT55), 70° C. (stLGT70), and 85° C. (stLGT85).

Stretched PLGA:PTMC blend had very similar degradation behavior to that of unstretched blend. FIG. 14A is a graphical representation of molecular weight normalized to the initial molecular weight (y-axis) for a 100% stretched 82.5:17.5 (wt:wt) PLGA:PTMC blend as function of degradation time (days; x-axis) at various testing temperatures. FIG. 14B is a graphical representation of mass normalized to the initial values (y-axis) for a 100% stretched 82.5:17.5 (wt:wt) PLGA:PTMC blend as a function of degradation time (days; x-axis) at various testing temperatures. Testing temperatures were 37° C. (stLGT37), 55° C. (stLGT55), 70° C. (stLGT70), and 85° C. (stLGT85).

Figure 15:
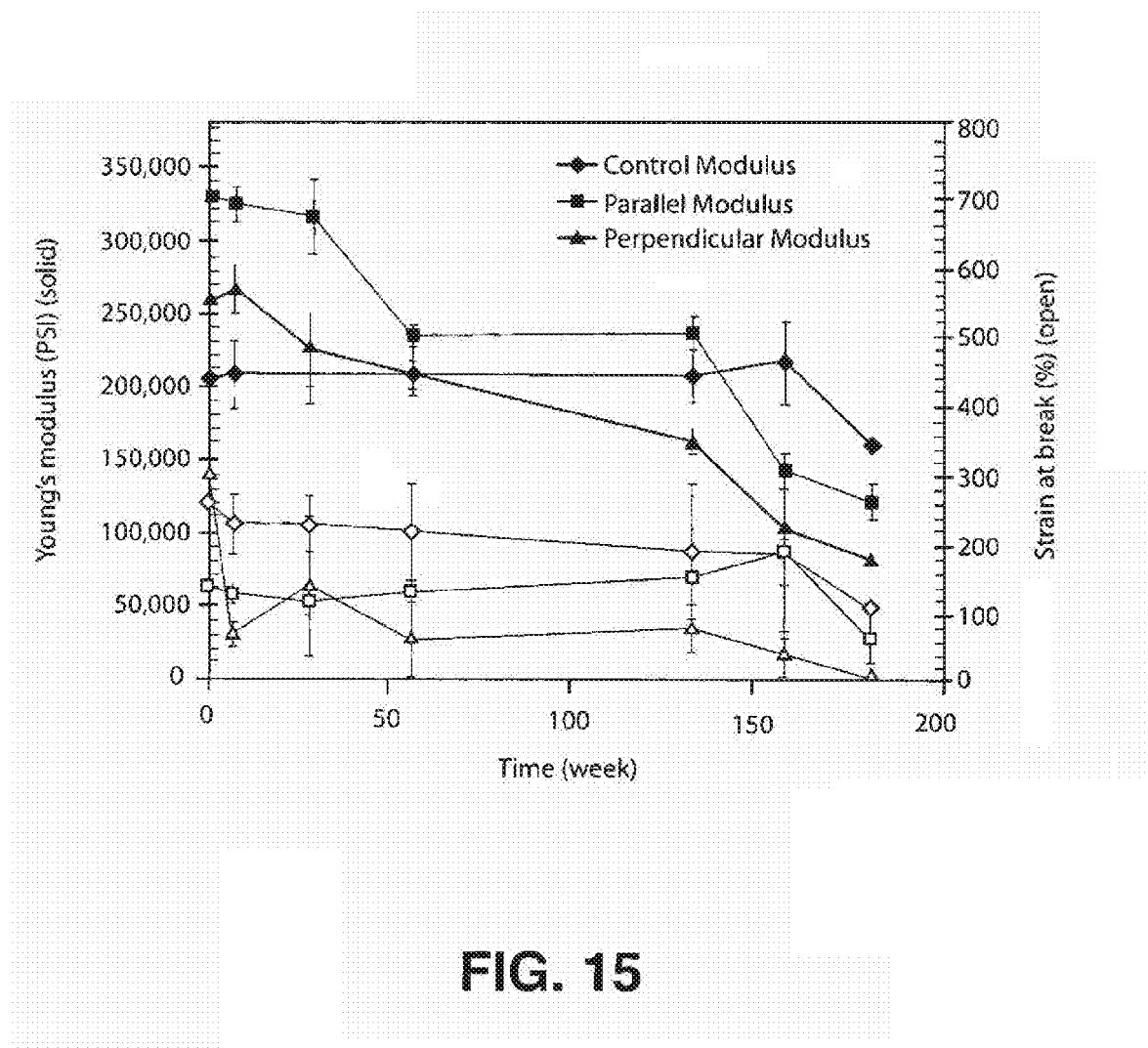
FIG. 15 is a graphical illustration showing mechanical properties (y-axes) after various degradation times (weeks; x-axis) for an unstretched PLGA:PTMC blend (circle) and a stretched PLGA:PTMC blend (square at the parallel direction and triangle at the perpendicular direction). Solid symbols indicate tensile modulus (pounds per square inch, PSI; left y-axis) and open symbols indicate strain at break (%; right y-axis).

Degradation induced changes of mechanical properties of stretched and unstretched PLGA:PTMC blends were tested according to ASTM D1708. Samples were taken out from degradation tests at various time points and tensile-tested at 37° C. in water batch (mounted to MTS). FIG. 15 is a graphical illustration showing mechanical properties (y-axes) after various degradation times (weeks; x-axis) for an unstretched PLGA:PTMC blend (circle) and a stretched PLGA:PTMC blend (square for parallel direction and triangle for perpendicular direction). Solid symbols indicate tensile modulus (pounds per square inch, PSI; left y-axis) and open symbols indicate strain at break (%; right y-axis). Initially, the modulus of stretched samples parallel to the stretching direction was higher than both the modulus tested perpendicular to the stretching direction and the modulus of unstretched samples. As degradation proceeded, the modulus of the unstretched samples remained similar. The modulus of the stretched samples decreased quickly, although the molecular weight and mass loss of both types of samples were very similar (e.g., FIGS. 12 and 14). Strain at break of all the samples did not substantially change within 5 months.

Figure 16A:
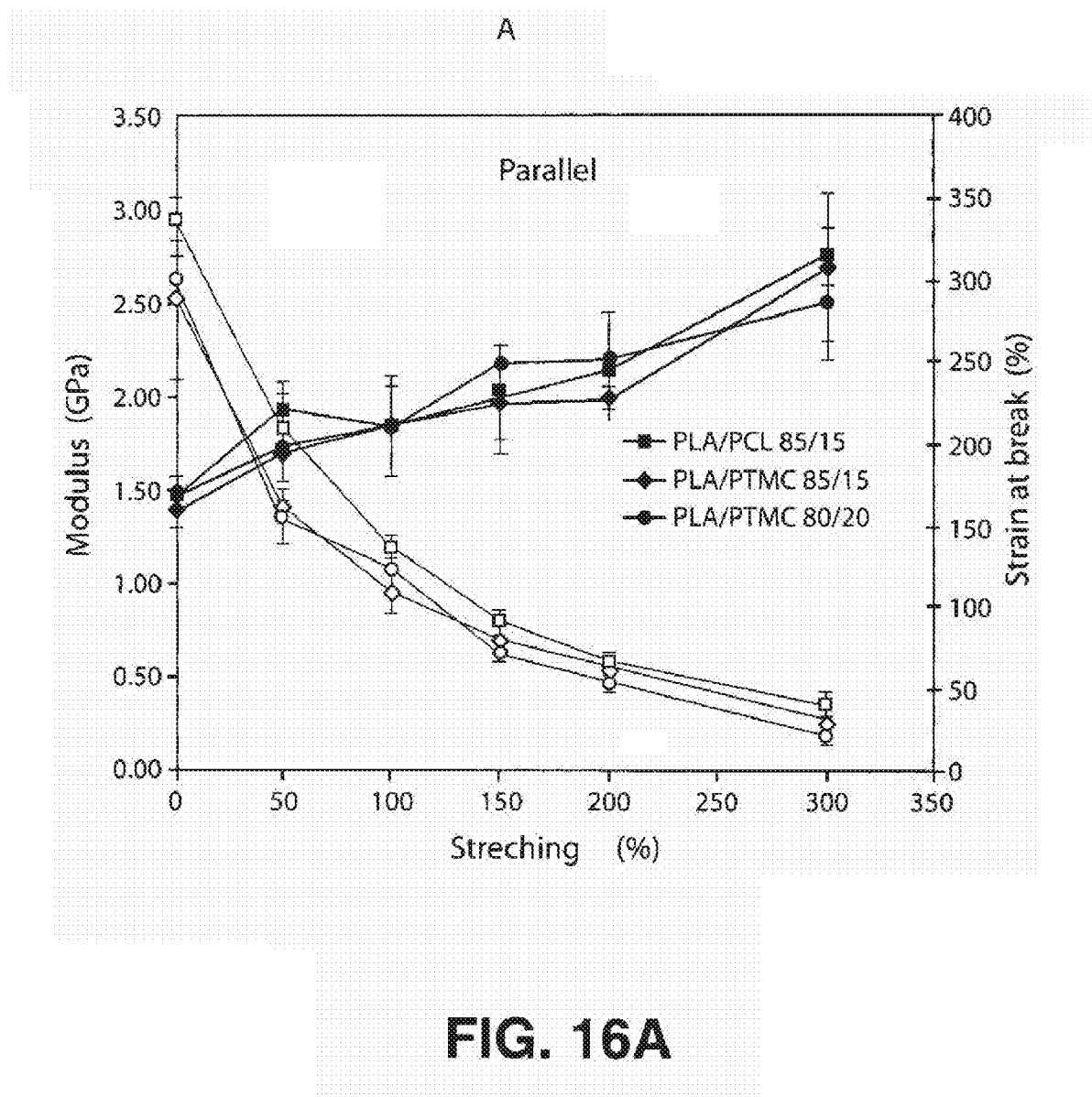
FIGS. 16A and 16B are graphical illustrations showing modulus (GPa; solid symbols, left y-axis) and strain at break (%; open symbols, right y-axis) of 85:15 (wt:wt) PLA:PCL (square), 85:15 (wt:wt) PLA:PTMC (diamond), and 80:20 (wt:wt) PLA:PTMC (triangle) blends (A) parallel to the stretching direction, and (B) perpendicular to the stretching direction, both as a function of stretching (%) value.
Figure 16B:
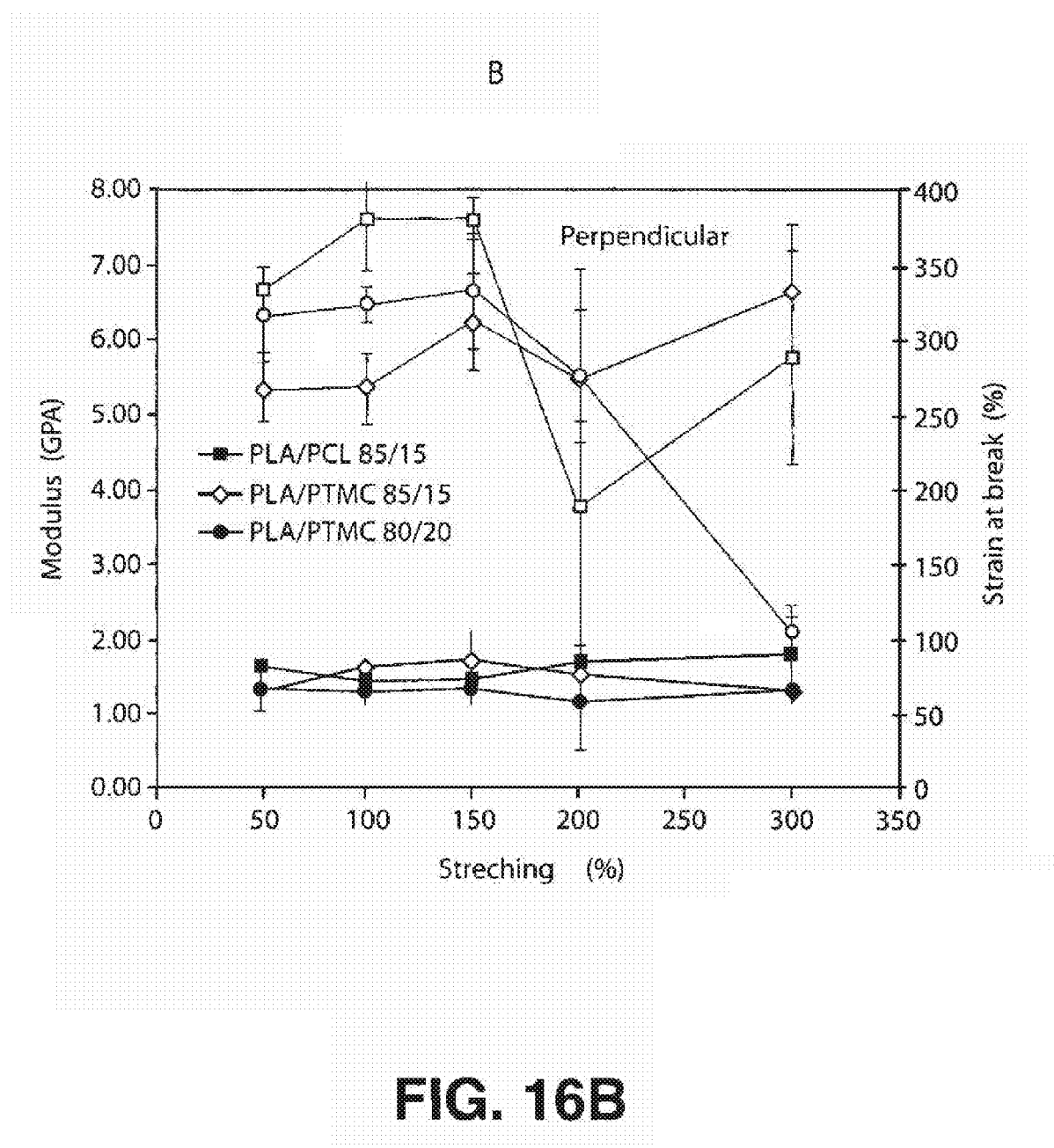

A combined reinforcement and toughening approach was also applied to a PLA:PCL blend (85:15, wt:wt) and PLA:PTMC blends (85:15 and 80:20, wt:wt). FIG. 16 shows the modulus (GPa; solid symbols, left y-axis) and strain at break (%; open symbols, right y-axis) (A) parallel to the stretching direction, and (B) perpendicular to the stretching direction, both as a function of stretching (%). The results were similar to those for PLGA:PTMC blends.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An implantable medical device comprising a polymer blend, the polymer blend comprising:
   a first phase that is continuous and that comprises a first biodegradable polymer having chains, the first phase having a glass transition temperature of at least 40° C., and wherein the chains of the first biodegradable polymer are oriented along an axis; and
   a second phase that is phase-separated from the first continuous phase and that comprises a second biodegradable polymer, the second phase having a glass transition temperature of 15° C. or less;
   wherein the modulus of the polymer blend parallel to the axis of orientation is at least 100% of the modulus of the first biodegradable polymer; and
   wherein the strain at break of the polymer blend parallel to the axis of orientation is at least 120% of the strain at break of the first biodegradable polymer.

2. An implantable medical device comprising a biodegradable polymer blend, the polymer blend comprising:
   a first phase that is continuous and that comprises a first biodegradable polymer having chains, the first phase having a glass transition temperature of at least 40° C., and wherein the chains of the first biodegradable polymer are oriented along an axis; and
   a second phase that is phase-separated from the first continuous phase and that comprises a second biodegradable polymer, the second phase having a glass transition temperature of 15° C. or less;
   wherein the modulus of the polymer blend parallel to the axis of orientation is at least 90% of the modulus of the first biodegradable polymer;
   wherein the strain at break of the polymer blend parallel to the axis of orientation is at least 120% of the strain at break of the first biodegradable polymer; and
   wherein the polymer blend comprises at least 5% by weight of the second phase, based on the total weight of the polymer blend.

3. An implantable medical device comprising a biodegradable polymer blend, the polymer blend comprising:
   a first phase that is continuous and that comprises a first biodegradable polymer having chains, the first phase having a glass transition temperature of at least 40° C., and wherein the chains of the first biodegradable polymer are oriented along an axis; and a second phase that is phase-separated from the first continuous phase and that comprises a second biodegradable polymer, the second phase having a glass transition temperature of 15° C. or less;

wherein the modulus of the polymer blend parallel to the axis of orientation is at least 80% of the modulus of the first biodegradable polymer;

wherein the strain at break of the polymer blend parallel to the axis of orientation is at least 120% of the strain at break of the first biodegradable polymer; and wherein the polymer blend comprises at least 20% by weight of the second phase, based on the total weight of the polymer blend.

4. A device according to claim 1 wherein the first phase has a glass transition temperature of at least 45° C.

5. A device according to claim 1 wherein the first phase has a glass transition temperature of at least 50° C.

6. A device according to claim 1 wherein the first phase has a glass transition temperature of at least 55° C.

7. A device according to claim 1 wherein the first phase has a glass transition temperature of at least 60° C.

8. A device according to claim 1 wherein the second phase has a glass transition temperature of 10° C. or less.

9. A device according to claim 1 wherein the second phase has a glass transition temperature of 5° C. or less.

10. A device according to claim 1 wherein the second phase has a glass transition temperature of 0° C. or less.

11. A device according to claim 1 wherein the second phase has a glass transition temperature of −5° C. or less.

12. A device according to claim 1 wherein the second phase has a glass transition temperature of −10° C. or less.

13. A device according to claim 1 wherein the strain at break of the polymer blend parallel to the axis of orientation is at least 150% of the strain at break of the first biodegradable polymer.

14. A device according to claim 1 wherein the strain at break of the polymer blend parallel to the axis of orientation is at least 200% of the strain at break of the first biodegradable polymer.

15. A device according to claim 1 wherein the strain at break of the polymer blend parallel to the axis of orientation is at least 300% of the strain at break of the first biodegradable polymer.

16. A device according to claim 1 wherein the modulus of the polymer blend parallel to the axis of orientation is at least 120% of the modulus of the first biodegradable polymer.

17. An implantable medical device according to claim 1, wherein the first phase comprises a polylactide homopolymer or copolymer having chains, and wherein the chains of the polylactide homopolymer or copolymer are oriented along an axis; and the second phase comprises a polymer selected from the group consisting of poly(trimethylene carbonate) (PTMC), polycaprolactone (PCL), polyhydroxybutyrate, and combinations thereof.

18. A device according to claim 17 wherein the polylactide homopolymer or copolymer is selected from the group consisting of poly(L-lactide) (PLLA), poly(D,L-lactide) (PDLLA), poly(L-lactide-co-D,L-lactide) (PLDLLA), poly (L-lactide-co-glycolide) (PLGA), poly(D,L-lactide-co-glycolide) (PDLGA), poly(lactide-co-caprolactone), poly(lactide-co-trimethylene carbonate), poly(lactide-co-hydroxybutyrate), poly(lactide-co-dioxane), and combinations thereof.

19. A device according to claim 1 wherein the polymer blend further comprises an additional component selected from the group consisting of a compatibilizer, a plasticizer, a bonding promoter, and combinations thereof.

20. A device according to claim 19 wherein the compatibilizer is a copolymer.

* * * * *